United States Patent [19]

Thomas et al.

[11] Patent Number: 5,614,393

[45] Date of Patent: Mar. 25, 1997

[54] PRODUCTION OF γ-LINOLENIC ACID BY A Δ6-DESATURASE

[75] Inventors: Terry L. Thomas, College Station; Avutu S. Reddy, Bryan; Michael Nuccio, College Station; Andrew N. Nunberg, Bryan, all of Tex.; Georges L. Freyssinet, Saint Cyr au mont d'or, France

[73] Assignee: Rhone-Poulenc Agrochimie, France

[21] Appl. No.: 366,779

[22] Filed: Dec. 30, 1994

Related U.S. Application Data

[63] Continuation-in-part of Ser. No. 307,382, Sep. 14, 1994, Pat. No. 5,552,306, which is a continuation of Ser. No. 959,952, Oct. 13, 1992, abandoned, which is a continuation-in-part of Ser. No. 817,919, Jan. 8, 1992, abandoned, which is a continuation-in-part of Ser. No. 774,475, Oct. 10, 1991, abandoned.

[51] Int. Cl.$^6$ .............. C12N 15/53; C12N 15/82; C12N 1/21; C12P 7/64
[52] U.S. Cl. .............. 435/134; 435/69.1; 435/70.1; 435/71.1; 435/172.3; 435/189; 435/325; 435/411; 435/412; 435/243; 435/252.3; 435/254.11; 435/320.1; 536/23.2; 536/23.6; 536/24.1; 800/205; 800/250; 800/255; 800/DIG. 14; 800/DIG. 17; 800/DIG. 23; 800/DIG. 26; 800/DIG. 56; 800/DIG. 43; 800/435; 800/414; 800/415; 800/416; 800/419
[58] Field of Search ............... 800/205, 250, 800/255, DIG. 14, DIG. 17, DIG. 23, DIG. 26, DIG. 43, DIG. 56; 435/69.1, 41, 134, 172.3, 240.4, 243, 252.3, 320.1, 70.1, 71.1, 189, 240.1, 240.45, 254.11; 536/23.6, 23.2, 24.1; 935/6, 14, 22, 24, 29, 30, 66–70, 72

[56] References Cited

U.S. PATENT DOCUMENTS 4,736,866  4/1988  Leder et al. .................. 800/1

FOREIGN PATENT DOCUMENTS

A0255378  2/1988  European Pat. Off. .
WO9010076  9/1990  WIPO .
WO94/18337  8/1994  WIPO .............. C12N 15/82

OTHER PUBLICATIONS

Galle, et al. (1995) "Solubilization of Δ12– and Δ6–Desaturases from Seeds of Borage Microsomes" in *Plant Lipid Metabolism; 11th International Meeting on Plant Lipids*, Paris, France, Jun. 16–Jul. 1, 1994, Kluwer Academic Publishers, Netherlands, pp. 509–511.

Schmidt, et al. (1995) "PCR–Based Cloning of Membrane–Bound Desaturases" in *Plant Lipid Metabolism; 11th International Meeting on Plant Lipids*, Paris, France, Jun. 26–Jul. 1, 1994, Kluwer Academic Publishers, Netherlands, pp. 21–23.

Griffiths, et al. (1988) "Δ6– and Δ12–Desaturase Activities and Phosphatidic Acid Formation in Microsomal Preparations from the Developing Cotyledons of Common Borage (*Borago officinalis*)" in *The Biochemical Journal* 252(3):641–647.

Galle, et al. (1993) "Biosynthesis of γ–Linolenic Acid in Developing Seeds of Borage (*Borago officinalis* L.)" in *Biochimica et Biophysica Acta* 1158:52–58.

Schmidt, et al. (1994) "Purification and PCR–Based cDNA Cloning of a Plastidial n–6 Desaturase" in *Plant Molecular Biology* 26:631–642.

Bafor, et al. (Apr. 1990) "Properties of the Glycerol Acylating Enzymes in Microsomal Preparations from the Developing Seeds of Safflower (*Carthamus tinctorius*) and Turnip Rape (*Brassica campestris*) and their Ability to Assemble Cocoa–Butter Type Fats" in *JAOCS* 67:217–225.

Kodama, et al. (1994) "Genetic Enhancement of Cold Tolerance by Expression of a Gene for Chloroplast ω–3 Fatty Acid Desaturase in Transgenic Tobacco" in *Plant Physiol.* 105:601–605.

H. Wada et al., Plant Cell Physiol. 30(7) ('89) 971–8.

S. Gibson et al., Plant, Cell, & Environ. 17(5) ('94) 627–37.

Aebersold et al (1987) "Internal amino acid sequence analysis of proteins separated by one or two–dimensional gel electrophoresis after in situ protease digestion on nitrocellulose," *Proc. Natl. Acad. Sci. USA* 84:6970–6974.

Brenner (1976) "Regulatory Function of Δ6–Desaturase—A Key Enzyme of Polyunsaturated Fatty Acid Synthesis," *Adv. Exp. Med. Biol.* 83:85–101.

Crozier, et al (1989) "Black Currant Seed Oil Feeding and Fatty Acid in Liver Lipid Classes of Guinea Pigs," *Lipids* 24:460–466.

Dahmer, et al. (1989) "A Rapid Screening Technique for Determining the Lipid Composition of Soybean Seed," *J. Amer. Oil Chem. Soc.* 66:543–548.

Devereux, et al (1984) "A Comprehensive Set of Sequence Analysis Programs for the VAX," *Nucleic Acids Res.* 12:387–395.

Golecki, et al (1982) "The Biology of the Cyanobacteria," (Eds. Carr and Whitton), pp. 125–141.

(List continued on next page.)

*Primary Examiner*—Charles C. P. Rories
*Attorney, Agent, or Firm*—Scully, Scott, Murphy & Presser

[57] ABSTRACT

Linoleic acid is converted into γ-linolenic acid by the enzyme Δ6-desaturase. The present invention is directed to isolated nucleic acids comprising the Δ6-desaturase gene. More particularly, the isolated nucleic acid comprises the promoter, coding region and termination regions of the Δ6-desaturase gene. The present invention provides recombinant constructions comprising the Δ6-desaturase coding region in functional combination with heterologous regulatory sequences. The nucleic acids and recombinant constructions of the instant invention are useful in the production of GLA in transgenic organisms.

44 Claims, 8 Drawing Sheets

OTHER PUBLICATIONS

Harpster et al (1988) "Relative strengths of the 35S cauliflower mosaic virus, 1', 2', and nopaline synthase promoters in transformed tobacco sugarbeet and oilseed rape callus tissue," *Mol. Gen. Genet* 212:182–190.

Horrobin et al (1984) "Effects of Essential Fatty Acids on Prostaglandin Biosynthesis," *Biomed. Biochim. Acta* 43:S114–S120.

Jaye et al (1983) "Isolation of a human anti–haemophilic factor IX cDNA clone using a unique 52–base synthetic oligonucleotide probe deduced from the amino acid sequence of bovine factor IX," *Nucleic Acids Research* 11(8):2325–2335.

Kenyon, et al (1972) "Fatty Acid Composition and Physiological Properties of Some Filamentous Blue–Green Algae," *Arch. Mikrobiol.* 83:216–236.

Kenyon (1972) "Fatty Acid Composition of Unicellular Strains of Blue Green Algae," *J. Bacteriology* 109:827–834.

Kyte, et al (1982) "A Simple Method for Displaying the Hydropathic Character of a Protein," *J. Mol. Biol.* 157:105–132.

Miguel, et al (1992) "Arabidopsis Mutants Deficient in Polyunsaturated Fatty Acid Synthesis," *J. Biol. Chem.* 267:1502–1509.

Murata, et al (1987) "Lipids of Blue Green Algae (Cyanobacteria)" In: Stumpf PK (eds) *The Biochemistry of Plants*, Academic Press, Orlando, FL 9:315–347.

Murata (1989) "Low–Temperature Effects on Cyanobacterial Membranes," *Journal of Bioenergetics and Biomembranes* 21:60–75.

Murphy, et al (1989) "Are the promoter regions of seed storage protein genes suitable for the expression of genes involved in storage lipid synthesis?," *Biochem. Soc. Transactions* 17:685–686.

Ohlrogge et al (1991) "The Genetics of Plant Lipids," *Biochim. Biophys. Acta.* 1982:1–26.

Ow, et al (1987) "Functional regions of the cauliflower mosaic virus 35S RNA promoter determined by use of the firefly luciferase gene as a reporter of promoter activity," *Proc. Natl. Acad. Sci. USA* 84:4870–4874.

Ripka, et al (1979) "Generic Assignments, Strain Histories and Properties of Pure Cultures of Cyanobacteria," *J. General Micro* 111:1–61.

Sanger et al (1977) "DNA Sequencing with Chain–Terminating Inhibitors," *Proc. Natl. Acad. Sci. USA* 74:5463–5467.

Shanklin, et al (1991) "Stearoyl–acyl–carrier–protein Desaturase from Higher Plants is Structurally Unrelated to the Animal and Fungal Homologs," *Proc. Natl. Acad. Sci., USA* 88:2510–2514.

Somerville, et al (1991) "Plant Lipids: Metabolism, Mutants, and Membranes," *Science* 252:80–87.

Stumpf (1987) "Plant Lipid Biotechnology Through the Looking Glass," *J. American Oil Chemical Society* 65:1641–1645.

Stymne, et al (1986) "Biosynthesis of γ–Linolenic Acid in Cotyledons and Microsomal Preparations of the Developing Seeds of Common Borage (*Borago officinalis*)," *Biochem. J.* 240:385–393.

Sugano, et al (1986) "Effects of Mold Oil Containing γ–Linolenic Acid on the Blood Cholesterol and Eicosanoid Levels in Rats," *Agric. Biol. Chem.* 50:2483–2491.

Wada, et al (1990) "Enhancement of Chilling Tolerance of a Cyanobacterium by Genetic Manipulation of Fatty Acid Desaturation," *Nature* 347:200–203. 2491.

Weete, J.D. (1980) *Lipid Biochemistry of Fungi and Other Organisms*, Plenum Press, New York, Chapter 6, 157–163.

Yadav, et al (1993) "Cloning of Higher Plant ω–3 Fatty Acid Desaturases," *Plant Physiology* 103:467–476.

FIG.5A

```
   1 aatatctgcc tacctcccca aagagagtag tcattttca tcaatgctg ctcaaatcaa gaaatacatt acctcagatg   80
  81 aactcaagaa ccacgataaa cccggagatc tatggatctc gattcaagg aaagcctatg atgtttcgga ttgggtgaaa  160
 161 gaccatccag gtggcagctt tccccttgaag agtcttgctg gtcaagagt aactgatgca tttgttgcat tccatcctgc  240
 241 ctctacatgg aagaatcttg ataagttttt cactgggtat tatcctctgt attactctgt ttctgaggtt tctaaagatt  320
 321 ataggaagct tgtgtttgag tttctaaaa tggcatatta ggtcatatta tgtttgcaac tttgtgcctt  400
 401 atagcaatgc tgtttgctat gagtgtttat ggggttttgt tttgtgagg tgtttggta cattgtttt ctggtgtttt  480
 481 gatgggtttt ctttggattc agagtggttg gattggacat agtgtctgat agtgtctgat tcaaggctta  560
 561 ataagtttat gggtatttt gctgcaaatt gtctttcagg aataagtatt ggttggtga aatgaaccaa taatgcacat  640
 641 cacattgcct gtaatagcct tgaatatgac cctgatttac attcctgtt gtgtcttcca agttttttgg  720
 721 ttcactcacc tctcattctt atgagaaaag gttgactttt gactctttat caagatcct gtaagttat caacattgga  800
 801 catttaccc tattatgtgt gctgctaggc tcaatatgta tgtacaatct ctcataatgt tgttgaccaa gagaaatgtg  880
 881 tcctatcgag ctcaggaact ctgggatgc cgattggta cccgttgctt cccgttgtt gttcctgtt tgcctaattg  960
 961 gggtgaaaga attatgtttg ttattgcaag tttatcagtg actggaatgc gttctccctg gtttctccttg aaccactct 1040
1041 cttcaagtgt ttatgttgga aagcctaaag ggaataattg gtttgagaaa caaacggatg ggacacttga cattctctgt 1120
1121 cctccctga tggattggtt tcatggtgga ttgcaattcc aaattgagca tcattgttt cccaagatgc ctagatgcaa 1200
1201 ccttaggaaa atctgcccct acgtgatcga gttatgcaag aaacataatt tgccttacaa ttatgcatct ttctccaagg 1280
1281 ccaatgaaat gacactccaga acattgagga acacagcatt gcaggctagg gatataacca agccgctccc gaagaatttg 1360
1361 gtatggaag ctcttcacac tcatgtaa aattacccct agttcatgta ataatttgag attatgtatc tcctatgttt 1440
1441 gtgtcttgtc ttgttggagt cattggcaact tgtcttttat ggttattag atgttttta atatattta 1520
1521 gaggtttgc ttcatctcc attattgatg aataaggagt tgcatattgt caattgttgt gctcaatatc tgatattttg 1600
1601 gaatgtactt tgtaccactg tgtttcagt tgaagctcat gtgtactcct atagactttg tttaatggt tatgtcatgt 1680
1681 tattt                                                                                   1685
```

FIG.5B

```
  1 MAAQIKKYIT SDELKNHDKP GDLWISIQGK AYDVSDWVKD HPGGSFPLKS LAGQEVTDAF VAFHPASTWK NLDKFFTGYY   80
 81 LKDYSVSEVS KDYRKLVFEF SKMGLYDKKG HIMFATLCFI AMLFAMSVYG VLFCEGVLVH LFSGCLMGFL WIQSGWIGHD  160
161 AGHYMVVSDS RLNKFMGIFA ANCLSGISIG WWKWNHNAHH IACNSLEYDP DLQYIPFLVV SSKFFGSLTS HFYEKRLTFD  240
241 SLSRFFVSYQ HWTFYPIMCA ARLNMYVQSL IMLLTKRNVS YRAQELLGCL VFSIWYPLLV SCLPNWGERI MFVIASLSVT  320
321 GMQQVQFSLN HFSSSVYVGK PKGNNWFEKQ TDGTLDISCP PWMDWFHGGL QFQIEHHLFP KMPRCNLRKI SPYVIELCKK  400
401 HNLPYNYASF SKANEMTLRT LRNTALQARD ITKPLPKNLV WEALHTHG                                     448
```

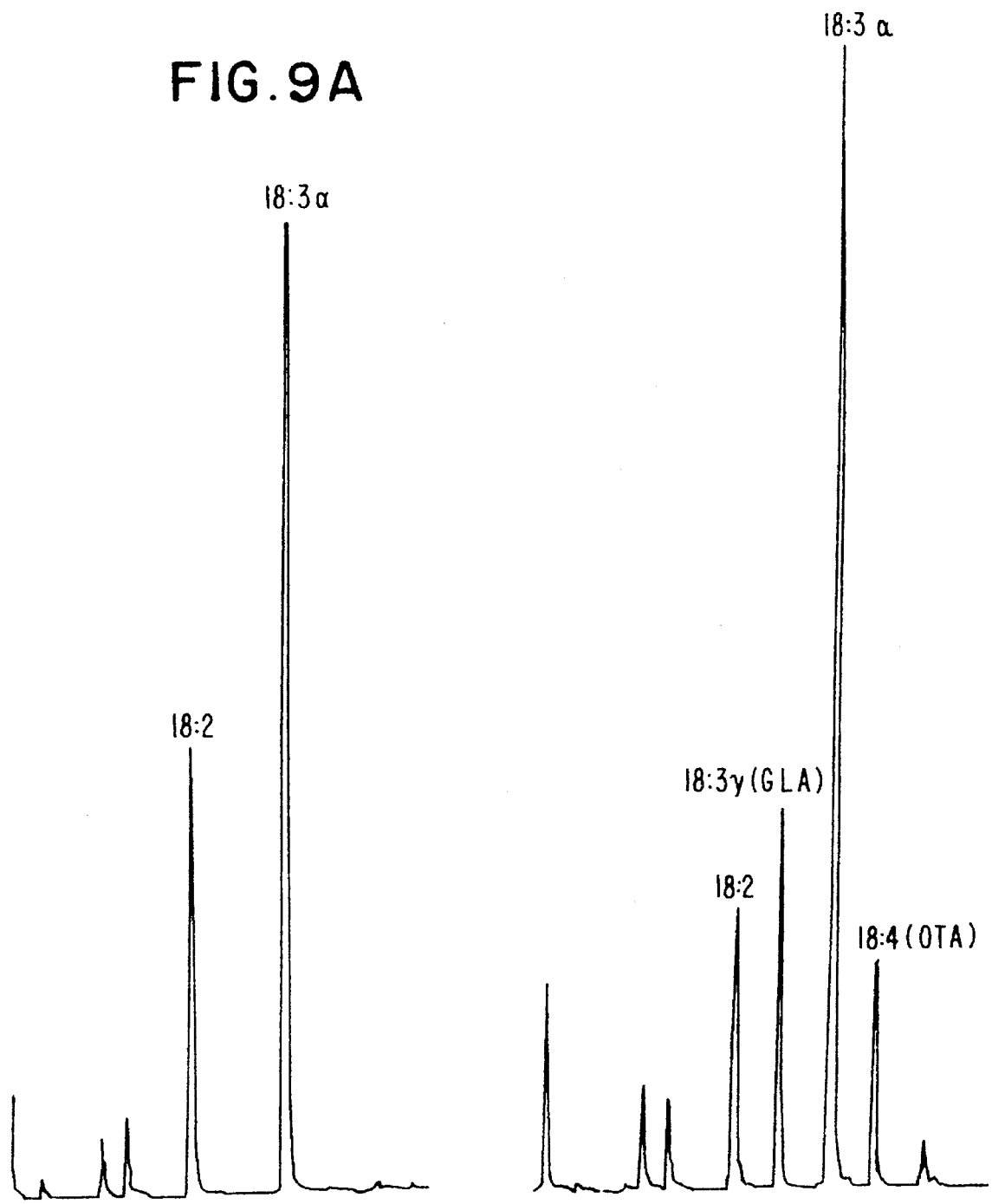

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 3588 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 2002..3081

( x i ) SEQUENCE DESCRIPTION: SEQ ID NO:1:

```
GCTAGCCACC  AGTGACGATG  CCTTGAATTT  GGCCATTCTG  ACCCAGGCCC  GTATTCTGAA     60
TCCCCGCATT  CGCATTGTTA  ATCGTTTGTT  CAACCATGCC  CTGGGTAAAC  GTTTAGACAC    120
CACCTTGCCA  GACCACGTTA  GTTGAGTGT   TTCCGCCCTG  GCGGCCCCGA  TTTTTTCCTT    180
TGCGGCTTTG  GGCAATCAGG  CGATCGGGCA  ATTGCGTTTG  TTTGACCAGA  CTTGGCCCAT    240
TCAGGAAATT  GTCATTCACC  AAGACCATCC  CTGGCTCAAT  TTACCCCTGG  CGGATTTATG    300
GGATGATCCG  AGCCGAATGT  TGATCTATTA  CCTACCGGCC  CACAGTGAAA  CGGATTTAGT    360
AGGCGCAGTG  GTGAATAATT  TAACGTTGCA  ATCTGGGGAC  CATTTAATAG  TGGGACAAAA    420
ACCCCAACCC  AAGACCAAAC  GGCGATCGCC  TTGGCGCAAA  TTTTCCAAAC  TGATTACCAA    480
CCTGCGGGAG  TATCAGCGGT  ATGTCCAACA  GGTGATATGG  GTGGTGTTGT  TTTTATTGTT    540
GATGATTTTT  CTGGCCACCT  TCATCTACGT  TTCCATTGAT  CAACATATTG  CCCAGTGGA     600
CGCGTTGTAT  TTTTCCGTGG  GCATGATTAC  CGGGGCCGGT  GGCAAGGAAG  AGGTGGCCGA    660
AAAGTCCCCC  GATATCATCA  AGTATTCAC   AGTGGTGATG  ATGATCGCCG  GGGCGGGGGT    720
GATTGGTATT  TGTTATGCCC  TACTGAATGA  TTTCATCCTT  GGCAGTCGCT  TTAGTCAGTT    780
TTTGGATGCG  GCCAAGTTAC  CCGATCGCCA  TCACATCATC  ATTTGTGGGC  TGGGGGGAGT    840
GAGCATGGCC  ATTATTGAAG  AGTTAATTCA  CCAGGGCCAT  GAAATTGTGG  TAATCGAAAA    900
GGATACAGAT  AATCGTTTCT  TGCATACGGC  CCGCTCCCTG  GGGGTGCCCG  TAATTGTGGA    960
GGATGCCCGC  CTAGAAAGAA  CGTTGGCCTG  CGCCAATATC  AACCGAGCCG  AAGCCATTGT   1020
GGTGGCCACC  AGCGACGACA  CCGTTAACTT  GGAAATTGGC  CTAACTGCCA  AGGCGATCGC   1080
CCCTAGCCTG  CCAGTGGTGT  TGCGTTGCCA  GGATGCCCAG  TTTAGCCTGT  CCCTGCAGGA   1140
AGTATTTGAA  TTTGAAACGG  TGCTTTGTCC  GGCGGAATTG  GCCACCTATT  CCTTTGCGGC   1200
GGCGGCCCTG  GGGGGCAAAA  TTTTGGGCAA  CGGCATGACC  GATGATTTGC  TGTGGGTAGC   1260
CCTAGCCACC  TTAATCACTC  CTAACCATCC  CTTTGCCGAC  CAATTGGTTA  AAATTGCAGC   1320
CCAAAAGTCT  GATTTCGTTC  CCCTCTATCT  AGAACGGGGT  GGCAAAACCA  TCCATAGCTG   1380
GGAATTATTG  GGTACCCATC  TCGACTCTGG  AGACGTGTTG  TATTTAACCA  TGCCCGCCAC   1440
TGCCCTAGAG  CAACTTTGGC  GATCGCCCCG  TGCCACTGCT  GATCCTCTGG  ACTCTTTTT    1500
GGTTTAGCAT  GGGGGGATGG  AACTCTTGAC  TCGGCCCAAT  GGTGATCAAG  AAAGAACGCT   1560
```

-continued

```
TTGTCTATGT  TTAGTATTTT  TAAGTTAACC  AACAGCAGAG  GATAACTTCC  AAAAGAAATT      1620

AAGCTCAAAA  AGTAGCAAAA  TAAGTTTAAT  TCATAACTGA  GTTTTACTGC  TAAACAGCGG      1680

TGCAAAAAAG  TCAGATAAAA  TAAAAGCTTC  ACTTCGGTTT  TATATTGTGA  CCATGGTTCC      1740

CAGGCATCTG  CTCTAGGGAG  TTTTTCCGCT  GCCTTTAGAG  AGTATTTTCT  CCAAGTCGGC      1800

TAACTCCCCC  ATTTTAGGC   AAAATCATAT  ACAGACTATC  CCAATATTGC  CAGAGCTTTG      1860

ATGACTCACT  GTAGAAGGCA  GACTAAAATT  CTAGCAATGG  ACTCCCAGTT  GGAATAAATT      1920

TTTAGTCTCC  CCCGGCGCTG  GAGTTTTTTT  GTAGTTAATG  GCGGTATAAT  GTGAAAGTTT      1980

TTTATCTATT  TAAATTTATA  A ATG CTA ACA GCG GAA AGA ATT AAA TTT ACC           2031
               Met Leu Thr Ala Glu Arg Ile Lys Phe Thr
                 1           5                    10
```

| | | | | | | | | | | | | | | | | |
|---|---|---|---|---|---|---|---|---|---|---|---|---|---|---|---|---|
| CAG | AAA | CGG | GGG | TTT | CGT | CGG | GTA | CTA | AAC | CAA | CGG | GTG | GAT | GCC | TAC | 2079 |
| Gln | Lys | Arg | Gly | Phe | Arg | Arg | Val | Leu | Asn | Gln | Arg | Val | Asp | Ala | Tyr | |
| | | | | 15 | | | | 20 | | | | | 25 | | | |
| TTT | GCC | GAG | CAT | GGC | CTG | ACC | CAA | AGG | GAT | AAT | CCC | TCC | ATG | TAT | CTG | 2127 |
| Phe | Ala | Glu | His | Gly | Leu | Thr | Gln | Arg | Asp | Asn | Pro | Ser | Met | Tyr | Leu | |
| | | | 30 | | | | 35 | | | | | 40 | | | | |
| AAA | ACC | CTG | ATT | ATT | GTG | CTC | TGG | TTG | TTT | TCC | GCT | TGG | GCC | TTT | GTG | 2175 |
| Lys | Thr | Leu | Ile | Ile | Val | Leu | Trp | Leu | Phe | Ser | Ala | Trp | Ala | Phe | Val | |
| | | | 45 | | | | 50 | | | | | 55 | | | | |
| CTT | TTT | GCT | CCA | GTT | ATT | TTT | CCG | GTG | CGC | CTA | CTG | GGT | TGT | ATG | GTT | 2223 |
| Leu | Phe | Ala | Pro | Val | Ile | Phe | Pro | Val | Arg | Leu | Leu | Gly | Cys | Met | Val | |
| | | | 60 | | | 65 | | | | | 70 | | | | | |
| TTG | GCG | ATC | GCC | TTG | GCG | GCC | TTT | TCC | TTC | AAT | GTC | GGC | CAC | GAT | GCC | 2271 |
| Leu | Ala | Ile | Ala | Leu | Ala | Ala | Phe | Ser | Phe | Asn | Val | Gly | His | Asp | Ala | |
| | 75 | | | | 80 | | | | 85 | | | | | 90 | | |
| AAC | CAC | AAT | GCC | TAT | TCC | TCC | AAT | CCC | CAC | ATC | AAC | CGG | GTT | CTG | GGC | 2319 |
| Asn | His | Asn | Ala | Tyr | Ser | Ser | Asn | Pro | His | Ile | Asn | Arg | Val | Leu | Gly | |
| | | | | 95 | | | | 100 | | | | | 105 | | | |
| ATG | ACC | TAC | GAT | TTT | GTC | GGG | TTA | TCT | AGT | TTT | CTT | TGG | CGC | TAT | CGC | 2367 |
| Met | Thr | Tyr | Asp | Phe | Val | Gly | Leu | Ser | Ser | Phe | Leu | Trp | Arg | Tyr | Arg | |
| | | | 110 | | | | 115 | | | | | 120 | | | | |
| CAC | AAC | TAT | TTG | CAC | CAC | ACC | TAC | ACC | AAT | ATT | CTT | GGC | CAT | GAC | GTG | 2415 |
| His | Asn | Tyr | Leu | His | His | Thr | Tyr | Thr | Asn | Ile | Leu | Gly | His | Asp | Val | |
| | | 125 | | | | 130 | | | | | 135 | | | | | |
| GAA | ATC | CAT | GGA | GAT | GGC | GCA | GTA | CGT | ATG | AGT | CCT | GAA | CAA | GAA | CAT | 2463 |
| Glu | Ile | His | Gly | Asp | Gly | Ala | Val | Arg | Met | Ser | Pro | Glu | Gln | Glu | His | |
| | 140 | | | | | 145 | | | | | 150 | | | | | |
| GTT | GGT | ATT | TAT | CGT | TTC | CAG | CAA | TTT | TAT | ATT | TGG | GGT | TTA | TAT | CTT | 2511 |
| Val | Gly | Ile | Tyr | Arg | Phe | Gln | Gln | Phe | Tyr | Ile | Trp | Gly | Leu | Tyr | Leu | |
| 155 | | | | | 160 | | | | 165 | | | | | 170 | | |
| TTC | ATT | CCC | TTT | TAT | TGG | TTT | CTC | TAC | GAT | GTC | TAC | CTA | GTG | CTT | AAT | 2559 |
| Phe | Ile | Pro | Phe | Tyr | Trp | Phe | Leu | Tyr | Asp | Val | Tyr | Leu | Val | Leu | Asn | |
| | | | | 175 | | | | 180 | | | | | 185 | | | |
| AAA | GGC | AAA | TAT | CAC | GAC | CAT | AAA | ATT | CCT | CCT | TTC | CAG | CCC | CTA | GAA | 2607 |
| Lys | Gly | Lys | Tyr | His | Asp | His | Lys | Ile | Pro | Pro | Phe | Gln | Pro | Leu | Glu | |
| | | | | 190 | | | | 195 | | | | | 200 | | | |
| TTA | GCT | AGT | TTG | CTA | GGG | ATT | AAG | CTA | TTA | TGG | CTC | GGC | TAC | GTT | TTC | 2655 |
| Leu | Ala | Ser | Leu | Leu | Gly | Ile | Lys | Leu | Leu | Trp | Leu | Gly | Tyr | Val | Phe | |
| | | 205 | | | | 210 | | | | | 215 | | | | | |
| GGC | TTA | CCT | CTG | GCT | CTG | GGC | TTT | TCC | ATT | CCT | GAA | GTA | TTA | ATT | GGT | 2703 |
| Gly | Leu | Pro | Leu | Ala | Leu | Gly | Phe | Ser | Ile | Pro | Glu | Val | Leu | Ile | Gly | |
| | | 220 | | | | 225 | | | | | 230 | | | | | |
| GCT | TCG | GTA | ACC | TAT | ATG | ACC | TAT | GGC | ATC | GTG | GTT | TGC | ACC | ATC | TTT | 2751 |
| Ala | Ser | Val | Thr | Tyr | Met | Thr | Tyr | Gly | Ile | Val | Val | Cys | Thr | Ile | Phe | |
| 235 | | | | | 240 | | | | 245 | | | | | 250 | | |
| ATG | CTG | GCC | CAT | GTG | TTG | GAA | TCA | ACT | GAA | TTT | CTC | ACC | CCC | GAT | GGT | 2799 |

|  |  |  |  |  |  |  |  |  |  |  |  |
|---|---|---|---|---|---|---|---|---|---|---|---|
| Met | Leu | Ala | His | Val<br>255 | Leu | Glu | Ser | Thr | Glu<br>260 | Phe | Leu | Thr | Pro | Asp<br>265 | Gly |

| GAA | TCC | GGT | GCC | ATT | GAT | GAC | GAG | TGG | GCT | ATT | TGC | CAA | ATT | CGT | ACC | 2847 |
|---|---|---|---|---|---|---|---|---|---|---|---|---|---|---|---|---|
| Glu | Ser | Gly | Ala<br>270 | Ile | Asp | Asp | Glu | Trp<br>275 | Ala | Ile | Cys | Gln | Ile<br>280 | Arg | Thr | |

| ACG | GCC | AAT | TTT | GCC | ACC | AAT | AAT | CCC | TTT | TGG | AAC | TGG | TTT | TGT | GGC | 2895 |
|---|---|---|---|---|---|---|---|---|---|---|---|---|---|---|---|---|
| Thr | Ala | Asn<br>285 | Phe | Ala | Thr | Asn | Asn<br>290 | Pro | Phe | Trp | Asn | Trp<br>295 | Phe | Cys | Gly | |

| GGT | TTA | AAT | CAC | CAA | GTT | ACC | CAC | CAT | CTT | TTC | CCC | AAT | ATT | TGT | CAT | 2943 |
|---|---|---|---|---|---|---|---|---|---|---|---|---|---|---|---|---|
| Gly | Leu | Asn | His<br>300 | Gln | Val | Thr | His<br>305 | His | Leu | Phe | Pro | Asn<br>310 | Ile | Cys | His | |

| ATT | CAC | TAT | CCC | CAA | TTG | GAA | AAT | ATT | ATT | AAG | GAT | GTT | TGC | CAA | GAG | 2991 |
|---|---|---|---|---|---|---|---|---|---|---|---|---|---|---|---|---|
| Ile<br>315 | His | Tyr | Pro | Gln | Leu<br>320 | Glu | Asn | Ile | Ile | Lys<br>325 | Asp | Val | Cys | Gln | Glu<br>330 | |

| TTT | GGT | GTG | GAA | TAT | AAA | GTT | TAT | CCC | ACC | TTC | AAA | GCG | GCG | ATC | GCC | 3039 |
|---|---|---|---|---|---|---|---|---|---|---|---|---|---|---|---|---|
| Phe | Gly | Val | Glu | Tyr<br>335 | Lys | Val | Tyr | Pro | Thr<br>340 | Phe | Lys | Ala | Ala | Ile<br>345 | Ala | |

| TCT | AAC | TAT | CGC | TGG | CTA | GAG | GCC | ATG | GGC | AAA | GCA | TCG | TGACATTGCC | 3088 |
|---|---|---|---|---|---|---|---|---|---|---|---|---|---|---|
| Ser | Asn | Tyr | Arg<br>350 | Trp | Leu | Glu | Ala | Met<br>355 | Gly | Lys | Ala | Ser | 360 | |

| TTGGGATTGA | AGCAAAATGG | CAAAATCCCT | CGTAAATCTA | TGATCGAAGC | CTTTCTGTTG | 3148 |
|---|---|---|---|---|---|---|
| CCCGCCGACC | AAATCCCCGA | TGCTGACCAA | AGGTTGATGT | TGGCATTGCT | CCAAACCCAC | 3208 |
| TTTGAGGGGG | TTCATTGGCC | GCAGTTTCAA | GCTGACCTAG | GAGGCAAAGA | TTGGGTGATT | 3268 |
| TTGCTCAAAT | CCGCTGGGAT | ATTGAAAGGC | TTCACCACCT | TTGGTTTCTA | CCCTGCTCAA | 3328 |
| TGGGAAGGAC | AAACCGTCAG | AATTGTTTAT | TCTGGTGACA | CCATCACCGA | CCCATCCATG | 3388 |
| TGGTCTAACC | CAGCCCTGGC | CAAGGCTTGG | ACCAAGGCCA | TGCAAATTCT | CCACGAGGCT | 3448 |
| AGGCCAGAAA | AATTATATTG | GCTCCTGATT | TCTTCCGGCT | ATCGCACCTA | CCGATTTTTG | 3508 |
| AGCATTTTTG | CCAAGGAATT | CTATCCCCAC | TATCTCCATC | CCACTCCCCC | GCCTGTACAA | 3568 |
| AATTTTATCC | ATCAGCTAGC |  |  |  |  | 3588 |

( 2 ) INFORMATION FOR SEQ ID NO:2:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met<br>1 | Leu | Thr | Ala | Glu<br>5 | Arg | Ile | Lys | Phe | Thr<br>10 | Gln | Lys | Arg | Gly | Phe<br>15 | Arg |
|---|---|---|---|---|---|---|---|---|---|---|---|---|---|---|---|
| Arg | Val | Leu | Asn<br>20 | Gln | Arg | Val | Asp | Ala<br>25 | Tyr | Phe | Ala | Glu | His<br>30 | Gly | Leu |
| Thr | Gln | Arg<br>35 | Asp | Asn | Pro | Ser | Met<br>40 | Tyr | Leu | Lys | Thr | Leu<br>45 | Ile | Ile | Val |
| Leu | Trp<br>50 | Leu | Phe | Ser | Ala | Trp<br>55 | Ala | Phe | Val | Leu | Phe<br>60 | Ala | Pro | Val | Ile |
| Phe<br>65 | Pro | Val | Arg | Leu | Leu<br>70 | Gly | Cys | Met | Val | Leu<br>75 | Ala | Ile | Ala | Leu | Ala<br>80 |
| Ala | Phe | Ser | Phe | Asn<br>85 | Val | Gly | His | Asp | Ala<br>90 | Asn | His | Asn | Ala | Tyr<br>95 | Ser |
| Ser | Asn | Pro | His<br>100 | Ile | Asn | Arg | Val | Leu<br>105 | Gly | Met | Thr | Tyr | Asp<br>110 | Phe | Val |
| Gly | Leu | Ser<br>115 | Ser | Phe | Leu | Trp | Arg<br>120 | Tyr | Arg | His | Asn | Tyr<br>125 | Leu | His | His |

| | | | | | | | | | | | | | | |
|---|---|---|---|---|---|---|---|---|---|---|---|---|---|---|
| Thr | Tyr 130 | Thr | Asn | Ile | Leu | Gly 135 | His | Asp | Val | Glu | Ile 140 | His | Gly | Asp | Gly |
| Ala 145 | Val | Arg | Met | Ser | Pro 150 | Glu | Gln | His | Val 155 | Gly | Ile | Tyr | Arg | Phe 160 |
| Gln | Gln | Phe | Tyr | Ile 165 | Trp | Gly | Leu | Tyr | Leu 170 | Phe | Ile | Pro | Phe 175 | Tyr | Trp |
| Phe | Leu | Tyr | Asp 180 | Val | Tyr | Leu | Val | Leu 185 | Asn | Lys | Gly | Lys | Tyr 190 | His | Asp |
| His | Lys | Ile 195 | Pro | Pro | Phe | Gln | Pro 200 | Leu | Glu | Leu | Ala | Ser 205 | Leu | Leu | Gly |
| Ile | Lys 210 | Leu | Leu | Trp | Leu | Gly 215 | Tyr | Val | Phe | Gly | Leu 220 | Pro | Leu | Ala | Leu |
| Gly 225 | Phe | Ser | Ile | Pro | Glu 230 | Val | Leu | Ile | Gly | Ala 235 | Ser | Val | Thr | Tyr | Met 240 |
| Thr | Tyr | Gly | Ile | Val 245 | Val | Cys | Thr | Ile | Phe 250 | Met | Leu | Ala | His | Val 255 | Leu |
| Glu | Ser | Thr | Glu 260 | Phe | Leu | Thr | Pro | Asp 265 | Gly | Glu | Ser | Gly | Ala 270 | Ile | Asp |
| Asp | Glu | Trp 275 | Ala | Ile | Cys | Gln | Ile 280 | Arg | Thr | Thr | Ala | Asn 285 | Phe | Ala | Thr |
| Asn | Asn 290 | Pro | Phe | Trp | Asn | Trp 295 | Phe | Cys | Gly | Gly | Leu 300 | Asn | His | Gln | Val |
| Thr 305 | His | His | Leu | Phe | Pro 310 | Asn | Ile | Cys | His | Ile 315 | His | Tyr | Pro | Gln | Leu 320 |
| Glu | Asn | Ile | Ile | Lys 325 | Asp | Val | Cys | Gln | Glu 330 | Phe | Gly | Val | Glu | Tyr 335 | Lys |
| Val | Tyr | Pro | Thr 340 | Phe | Lys | Ala | Ala | Ile 345 | Ala | Ser | Asn | Tyr | Arg 350 | Trp | Leu |
| Glu | Ala | Met | Gly 355 | Lys | Ala | Ser | | | | | | | | | |

( 2 ) INFORMATION FOR SEQ ID NO:3:

( i ) SEQUENCE CHARACTERISTICS:
        ( A ) LENGTH: 1884 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

```
AGCTTCACTT CGGTTTTATA TTGTGACCAT GGTTCCCAGG CATCTGCTCT AGGGAGTTTT      60
TCCGCTGCCT TTAGAGAGTA TTTTCTCCAA GTCGGCTAAC TCCCCCATTT TTAGGCAAAA     120
TCATATACAG ACTATCCCAA TATTGCCAGA GCTTTGATGA CTCACTGTAG AAGGCAGACT     180
AAAATTCTAG CAATGGACTC CCAGTTGGAA TAAATTTTTA GTCTCCCCCG GCGCTGGAGT     240
TTTTTTGTAG TTAATGGCGG TATAATGTGA AAGTTTTTA TCTATTTAAA TTTATAAATG     300
CTAACAGCGG AAAGAATTAA ATTTACCCAG AAACGGGGGT TTCGTCGGGT ACTAAACCAA     360
CGGGTGGATG CCTACTTTGC CGAGCATGGC CTGACCCAAA GGGATAATCC CTCCATGTAT     420
CTGAAAACCC TGATTATTGT GCTCTGGTTG TTTTCCGCTT GGGCCTTTGT GCTTTTTGCT     480
CCAGTTATTT TTCCGGTGCG CCTACTGGGT TGTATGGTTT TGGCGATCGC CTTGGCGGCC     540
TTTTCCTTCA ATGTCGGCCA CGATGCCAAC CACAATGCCT ATTCCTCCAA TCCCCACATC     600
AACCGGGTTC TGGGCATGAC CTACGATTTT GTCGGGTTAT CTAGTTTTCT TTGGCGCTAT     660
```

| | | | | | | |
|---|---|---|---|---|---|---|
|CGCCACAACT|ATTTGCACCA|CACCTACACC|AATATTCTTG|GCCATGACGT|GGAAATCCAT|720|
|GGAGATGGCG|CAGTACGTAT|GAGTCCTGAA|CAAGAACATG|TTGGTATTTA|TCGTTTCCAG|780|
|CAATTTTATA|TTTGGGGTTT|ATATCTTTTC|ATTCCCTTTT|ATTGGTTTCT|CTACGATGTC|840|
|TACCTAGTGC|TTAATAAAGG|CAAATATCAC|GACCATAAAA|TTCCTCCTTT|CCAGCCCCTA|900|
|GAATTAGCTA|GTTTGCTAGG|GATTAAGCTA|TTATGGCTCG|GCTACGTTTT|CGGCTTACCT|960|
|CTGGCTCTGG|GCTTTTCCAT|TCCTGAAGTA|TTAATTGGTG|CTTCGGTAAC|CTATATGACC|1020|
|TATGGCATCG|TGGTTTGCAC|CATCTTTATG|CTGGCCCATG|TGTTGGAATC|AACTGAATTT|1080|
|CTCACCCCCG|ATGGTGAATC|CGGTGCCATT|GATGACGAGT|GGGCTATTTG|CCAAATTCGT|1140|
|ACCACGGCCA|ATTTTGCCAC|CAATAATCCC|TTTTGGAACT|GGTTTTGTGG|CGGTTTAAAT|1200|
|CACCAAGTTA|CCCACCATCT|TTTCCCCAAT|ATTTGTCATA|TTCACTATCC|CCAATTGGAA|1260|
|AATATTATTA|AGGATGTTTG|CCAAGAGTTT|GGTGTGGAAT|ATAAAGTTTA|TCCCACCTTC|1320|
|AAAGCGGCGA|TCGCCTCTAA|CTATCGCTGG|CTAGAGGCCA|TGGGCAAAGC|ATCGTGACAT|1380|
|TGCCTTGGGA|TTGAAGCAAA|ATGGCAAAAT|CCCTCGTAAA|TCTATGATCG|AAGCCTTTCT|1440|
|GTTGCCCGCC|GACCAAATCC|CCGATGCTGA|CCAAGGTTG|ATGTTGGCAT|TGCTCCAAAC|1500|
|CCACTTGAG|GGGGTTCATT|GGCCGCAGTT|TCAAGCTGAC|CTAGGAGGCA|AAGATTGGGT|1560|
|GATTTGCTC|AAATCCGCTG|GGATATTGAA|AGGCTTCACC|ACCTTTGGTT|CTACCCTGC|1620|
|TCAATGGGAA|GGACAAACCG|TCAGAATTGT|TTATTCTGGT|GACACCATCA|CCGACCCATC|1680|
|CATGTGGTCT|AACCCAGCCC|TGGCCAAGGC|TTGGACCAAG|GCCATGCAAA|TTCTCCACGA|1740|
|GGCTAGGCCA|GAAAAATTAT|ATTGGCTCCT|GATTCTTCC|GGCTATCGCA|CCTACCGATT|1800|
|TTTGAGCATT|TTTGCCAAGG|AATTCTATCC|CCACTATCTC|CATCCCACTC|CCCCGCCTGT|1860|
|ACAAAATTTT|ATCCATCAGC|TAGC| | | |1884|

(2) INFORMATION FOR SEQ ID NO:4:

(i) SEQUENCE CHARACTERISTICS:
        (A) LENGTH: 1685 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:4:

| | | | | | | |
|---|---|---|---|---|---|---|
|AATATCTGCC|TACCCTCCCA|AAGAGAGTAG|TCATTTTTCA|TCAATGGCTG|CTCAAATCAA|60|
|GAAATACATT|ACCTCAGATG|AACTCAAGAA|CCACGATAAA|CCCGGAGATC|TATGGATCTC|120|
|GATTCAAGGG|AAAGCCTATG|ATGTTTCGGA|TTGGGTGAAA|GACCATCCAG|GTGGCAGCTT|180|
|TCCCTTGAAG|AGTCTTGCTG|GTCAAGAGGT|AACTGATGCA|TTTGTTGCAT|TCCATCCTGC|240|
|CTCTACATGG|AAGAATCTTG|ATAAGTTTTT|CACTGGGTAT|TATCTTAAAG|ATTACTCTGT|300|
|TTCTGAGGTT|TCTAAAGATT|ATAGGAAGCT|TGTGTTTGAG|TTTTCTAAAA|TGGGTTTGTA|360|
|TGACAAAAAA|GGTCATATTA|TGTTTGCAAC|TTTGTGCTTT|ATAGCAATGC|TGTTTGCTAT|420|
|GAGTGTTTAT|GGGGTTTTGT|TTTGTGAGGG|TGTTTTGGTA|CATTTGTTTT|CTGGGTGTTT|480|
|GATGGGGTTT|CTTTGGATTC|AGAGTGGTTG|GATTGGACAT|GATGCTGGGC|ATTATATGGT|540|
|AGTGTCTGAT|TCAAGGCTTA|ATAAGTTTAT|GGGTATTTTT|GCTGCAAATT|GTCTTTCAGG|600|
|AATAAGTATT|GGTTGGTGGA|AATGGAACCA|TAATGCACAT|CACATTGCCT|GTAATAGCCT|660|
|TGAATATGAC|CCTGATTTAC|AATATATACC|ATTCCTTGTT|GTGTCTTCCA|AGTTTTTTGG|720|

| | | | | | |
|---|---|---|---|---|---|
| TTCACTCACC | TCTCATTTCT | ATGAGAAAAG | GTTGACTTTT | GACTCTTTAT | CAAGATTCTT | 780 |
| TGTAAGTTAT | CAACATTGGA | CATTTTACCC | TATTATGTGT | GCTGCTAGGC | TCAATATGTA | 840 |
| TGTACAATCT | CTCATAATGT | TGTTGACCAA | GAGAAATGTG | TCCTATCGAG | CTCAGGAACT | 900 |
| CTTGGGATGC | CTAGTGTTCT | CGATTTGGTA | CCCGTTGCTT | GTTTCTTGTT | TGCCTAATTG | 960 |
| GGGTGAAAGA | ATTATGTTTG | TTATTGCAAG | TTTATCAGTG | ACTGGAATGC | AACAAGTTCA | 1020 |
| GTTCTCCTTG | AACCACTTCT | CTTCAAGTGT | TTATGTTGGA | AAGCCTAAAG | GAATAATTG | 1080 |
| GTTTGAGAAA | CAAACGGATG | GGACACTTGA | CATTTCTTGT | CCTCCTTGGA | TGGATTGGTT | 1140 |
| TCATGGTGGA | TTGCAATTCC | AAATTGAGCA | TCATTTGTTT | CCCAAGATGC | CTAGATGCAA | 1200 |
| CCTTAGGAAA | ATCTCGCCCT | ACGTGATCGA | GTTATGCAAG | AAACATAATT | TGCCTTACAA | 1260 |
| TTATGCATCT | TTCTCCAAGG | CCAATGAAAT | GACACTCAGA | ACATTGAGGA | ACACAGCATT | 1320 |
| GCAGGCTAGG | GATATAACCA | AGCCGCTCCC | GAAGAATTTG | GTATGGGAAG | CTCTTCACAC | 1380 |
| TCATGGTTAA | AATTACCCTT | AGTTCATGTA | ATAATTTGAG | ATTATGTATC | TCCTATGTTT | 1440 |
| GTGTCTTGTC | TTGGTTCTAC | TTGTTGGAGT | CATTGCAACT | TGTCTTTTAT | GGTTTATTAG | 1500 |
| ATGTTTTTTA | ATATATTTTA | GAGGTTTTGC | TTTCATCTCC | ATTATTGATG | AATAAGGAGT | 1560 |
| TGCATATTGT | CAATTGTTGT | GCTCAATATC | TGATATTTTG | GAATGTACTT | TGTACCACTG | 1620 |
| TGTTTTCAGT | TGAAGCTCAT | GTGTACTTCT | ATAGACTTTG | TTTAAATGGT | TATGTCATGT | 1680 |
| TATTT | | | | | | 1685 |

(2) INFORMATION FOR SEQ ID NO:5:

(i) SEQUENCE CHARACTERISTICS:
(A) LENGTH: 448 amino acids
(B) TYPE: amino acid
(D) TOPOLOGY: linear (ii) MOLECULE TYPE: DNA (genomic)

(xi) SEQUENCE DESCRIPTION: SEQ ID NO:5:

```
Met Ala Ala Gln Ile Lys Lys Tyr Ile Thr Ser Asp Glu Leu Lys Asn
 1               5                  10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
```

```
                         180                           185                           190
Lys  Trp  Asn  His  Asn  Ala  His  His  Ile  Ala  Cys  Asn  Ser  Leu  Glu  Tyr
               195                      200                      205

Asp  Pro  Asp  Leu  Gln  Tyr  Ile  Pro  Phe  Leu  Val  Val  Ser  Ser  Lys  Phe
     210                      215                      220

Phe  Gly  Ser  Leu  Thr  Ser  His  Phe  Tyr  Glu  Lys  Arg  Leu  Thr  Phe  Asp
225                           230                      235                     240

Ser  Leu  Ser  Arg  Phe  Phe  Val  Ser  Tyr  Gln  His  Trp  Thr  Phe  Tyr  Pro
                    245                      250                           255

Ile  Met  Cys  Ala  Ala  Arg  Leu  Asn  Met  Tyr  Val  Gln  Ser  Leu  Ile  Met
               260                      265                      270

Leu  Leu  Thr  Lys  Arg  Asn  Val  Ser  Tyr  Arg  Ala  Gln  Glu  Leu  Leu  Gly
          275                      280                      285

Cys  Leu  Val  Phe  Ser  Ile  Trp  Tyr  Pro  Leu  Leu  Val  Ser  Cys  Leu  Pro
     290                      295                      300

Asn  Trp  Gly  Glu  Arg  Ile  Met  Phe  Val  Ile  Ala  Ser  Leu  Ser  Val  Thr
305                           310                      315                     320

Gly  Met  Gln  Gln  Val  Gln  Phe  Ser  Leu  Asn  His  Phe  Ser  Ser  Ser  Val
                    325                      330                      335

Tyr  Val  Gly  Lys  Pro  Lys  Gly  Asn  Asn  Trp  Phe  Glu  Lys  Gln  Thr  Asp
               340                      345                      350

Gly  Thr  Leu  Asp  Ile  Ser  Cys  Pro  Pro  Trp  Met  Asp  Trp  Phe  His  Gly
          355                      360                      365

Gly  Ser  Gln  Phe  Gln  Ile  Glu  His  His  Leu  Phe  Pro  Lys  Met  Pro  Arg
     370                      375                      380

Cys  Asn  Leu  Arg  Lys  Ile  Ser  Pro  Tyr  Val  Ile  Glu  Leu  Cys  Lys  Lys
385                           390                      395                     400

His  Asn  Leu  Pro  Tyr  Asn  Tyr  Ala  Ser  Phe  Ser  Lys  Ala  Asn  Glu  Met
               405                      410                      415

Thr  Leu  Arg  Thr  Leu  Arg  Asn  Thr  Ala  Leu  Gln  Ala  Arg  Asp  Ile  Thr
          420                      425                      430

Lys  Pro  Leu  Pro  Lys  Asn  Leu  Val  Trp  Glu  Ala  Leu  His  Thr  His  Gly
          435                      440                      445
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:6:

```
Trp  Ile  Gly  His  Asp  Ala  Gly  His
 1                  5
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:7:

```
Asn  Val  Gly  His  Asp  Ala  Asn  His
 1                  5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:8:

Val Leu Gly His Asp Cys Gly His
 1                5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:9:

Val Ile Ala His Glu Cys Gly His
 1                5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:10:

Val Ile Gly His Asp Cys Ala His
 1                5

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:11:

Val Val Gly His Asp Cys Gly His
 1                5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:12:

His Asn Ala His His
 1            5

( 2 ) INFORMATION FOR SEQ ID NO:13:

( i ) SEQUENCE CHARACTERISTICS:
        ( A ) LENGTH: 6 amino acids ( B ) TYPE: amino acid
        ( D ) TOPOLOGY: linear ( i i ) MOLECULE TYPE: DNA (genomic)

( x i ) SEQUENCE DESCRIPTION: SEQ ID NO:13:

His Asn Tyr Leu His His
 1                   5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:14:

His Arg Thr His His
 1               5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:15:

His Arg Arg His His
 1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:16:

His Asp Arg His His
 1               5

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:17:

His Asp Gln His His
 1               5

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: DNA (genomic)

( x i ) SEQUENCE DESCRIPTION: SEQ ID NO:18:

His Asp His His His
 1               5

( 2 ) INFORMATION FOR SEQ ID NO:19:

( i ) SEQUENCE CHARACTERISTICS:
       ( A ) LENGTH: 5 amino acids
       ( B ) TYPE: amino acid
       ( D ) TOPOLOGY: linear ( i i ) MOLECULE TYPE: DNA (genomic)

( x i ) SEQUENCE DESCRIPTION: SEQ ID NO:19:

His Asn His His His
 1               5

( 2 ) INFORMATION FOR SEQ ID NO:20:

( i ) SEQUENCE CHARACTERISTICS:
       ( A ) LENGTH: 6 amino acids
       ( B ) TYPE: amino acid
       ( D ) TOPOLOGY: linear ( i i ) MOLECULE TYPE: DNA (genomic)

( x i ) SEQUENCE DESCRIPTION: SEQ ID NO:20:

Phe Gln Ile Glu His His
 1               5

( 2 ) INFORMATION FOR SEQ ID NO:21:

( i ) SEQUENCE CHARACTERISTICS:
       ( A ) LENGTH: 6 amino acids
       ( B ) TYPE: amino acid
       ( D ) TOPOLOGY: linear ( i i ) MOLECULE TYPE: DNA (genomic)

( x i ) SEQUENCE DESCRIPTION: SEQ ID NO:21:

His Gln Val Thr His His
 1               5

( 2 ) INFORMATION FOR SEQ ID NO:22:

( i ) SEQUENCE CHARACTERISTICS:
       ( A ) LENGTH: 5 amino acids
       ( B ) TYPE: amino acid
       ( D ) TOPOLOGY: linear ( i i ) MOLECULE TYPE: DNA (genomic)

( x i ) SEQUENCE DESCRIPTION: SEQ ID NO:22:

His Val Ile His His
 1               5

( 2 ) INFORMATION FOR SEQ ID NO:23:

( i ) SEQUENCE CHARACTERISTICS:
       ( A ) LENGTH: 5 amino acids
       ( B ) TYPE: amino acid
       ( D ) TOPOLOGY: linear ( i i ) MOLECULE TYPE: DNA (genomic)

( x i ) SEQUENCE DESCRIPTION: SEQ ID NO:23:

His Val Ala His His
 1               5

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (ii) MOLECULE TYPE: DNA (genomic)

(xi) SEQUENCE DESCRIPTION: SEQ ID NO:24:

His Ile Pro His His
 1               5

(2) INFORMATION FOR SEQ ID NO:25:

(i) SEQUENCE CHARACTERISTICS:
        (A) LENGTH: 5 amino acids
        (B) TYPE: amino acid
        (D) TOPOLOGY: linear (ii) MOLECULE TYPE: DNA (genomic)

(xi) SEQUENCE DESCRIPTION: SEQ ID NO:25:

His Val Pro His His
 1               5

PRODUCTION OF γ-LINOLENIC ACID BY A Δ6-DESATURASE

This is a continuation-in-part of U.S. Ser. No. 08/307,382, filed Sep. 14, 1994, now U.S. Pat. No. 5,552,306, issued Sep. 3, 1996, which is a continuation of U.S. Ser. No. 07/959,952 filed Oct. 13, 1992, now abandoned, which is a continuation-in-part of U.S. Ser. No. 817,919, filed Jan. 8, 1992, now abandoned, which is a continuation-in-part application of U.S. Ser. No. 774,475 filed Oct. 10, 1991, now abandoned.

FIELD OF THE INVENTION

Linoleic acid (18:2) (LA) is transformed into gamma linolenic acid (18:3) (GLA) by the enzyme Δ6-desaturase. When this enzyme, or the nucleic acid encoding it, is transferred into LA-producing cells, GLA is produced. The present invention provides nucleic acids comprising the Δ6-desaturase gene. More specifically, the nucleic acids comprise the promoters, coding regions and termination regions of the Δ6-desaturase genes. The present invention is further directed to recombinant constructions comprising a Δ6-desaturase coding region in functional combination with heterologous regulatory sequences. The nucleic acids and recombinant constructions of the instant invention are useful in the production of GLA in transgenic organisms.

BACKGROUND OF THE INVENTION

Unsaturated fatty acids such as linoleic ($C_{18}\Delta^{9,12}$) and α-linolenic ($C_{18}\Delta^{9,12,15}$) acids are essential dietary constituents that cannot be synthesized by vertebrates since vertebrate cells can introduce double bonds at the $\Delta^9$ position of fatty acids but cannot introduce additional double bonds between the $\Delta^9$ double bond and the methyl-terminus of the fatty acid chain. Because they are precursors of other products, linoleic and α-linolenic acids are essential fatty acids, and are usually obtained from plant sources. Linoleic acid can be converted by mammals into γ-linolenic acid (GLA, $C_{18}\Delta^{6,9,12}$) which can in turn be converted to arachidonic acid (20:4), a critically important fatty acid since it is an essential precursor of most prostaglandins.

The dietary provision of linoleic acid, by virtue of its resulting conversion to GLA and arachidonic acid, satisfies the dietary need for GLA and arachidonic acid. However, a relationship has been demonstrated between consumption of saturated fats and health risks such as hypercholesterolemia, atherosclerosis and other clinical disorders which correlate with susceptibility to coronary disease, while the consumption of unsaturated fats has been associated with decreased blood cholesterol concentration and reduced risk of atherosclerosis. The therapeutic benefits of dietary GLA may result from GLA being a precursor to arachidonic acid and thus subsequently contributing to prostaglandin synthesis. Accordingly, consumption of the more unsaturated GLA, rather than linoleic acid, has potential health benefits. However, GLA is not present in virtually any commercially grown crop plant.

Linoleic acid is converted into GLA by the enzyme Δ6-desaturase. Δ6-desaturase, an enzyme of more than 350 amino acids, has a membrane-bound domain and an active site for desaturation of fatty acids. When this enzyme is transferred into cells which endogenously produce linoleic acid but not GLA, GLA is produced. The present invention, by providing the gene encoding Δ6-desaturase, allows the production of transgenic organisms which contain functional Δ6-desaturase and which produce GLA. In addition to allowing production of large amounts of GLA, the present invention provides new dietary sources of GLA.

SUMMARY OF THE INVENTION

The present invention is directed to isolated Δ6-desaturase genes. Specifically, the isolated genes comprises the Δ6-desaturase promoters, coding regions, and termination regions.

The present invention is further directed to expression vectors comprising the Δ6-desaturase promoter, coding region and termination region.

Yet another aspect of this invention is directed to expression vectors comprising a Δ6-desaturase coding region in functional combination with heterologous regulatory regions, i.e. elements not derived from the Δ6-desaturase gene.

Cells and organisms comprising the vectors of the present invention, and progeny of such organisms, are also provided by the present invention.

A further aspect of the present invention provides isolated bacterial Δ6-desaturase. An isolated plant Δ6-desaturase is also provided.

Yet another aspect of this invention provides a method for producing plants with increased gamma linolenic acid content.

A method for producing chilling tolerant plants is also provided by the present invention.

BRIEF DESCRIPTION OF THE DRAWINGS

FIG. 5A depicts the DNA sequence of a Δ-6 desaturase cDNA isolated from borage.

FIG. 5B depicts the protein sequence of the open reading frame in the isolated borage Δ-6 desaturase cDNA. Three amino acid motifs characteristic of desaturases are indicated and are, in order, lipid box, metal box 1, and metal box 2.

FIG. 9(A and B) provides gas liquid chromatography profiles of an untransformed tobacco leaf (Panel A) and a tobacco leaf transformed with 121.Δ6.NOS. The positions of 18:2, 18:3 a, 18:3γ(GLA), and 18:4 are indicated.

DETAILED DESCRIPTION OF THE INVENTION

Figure 1A:
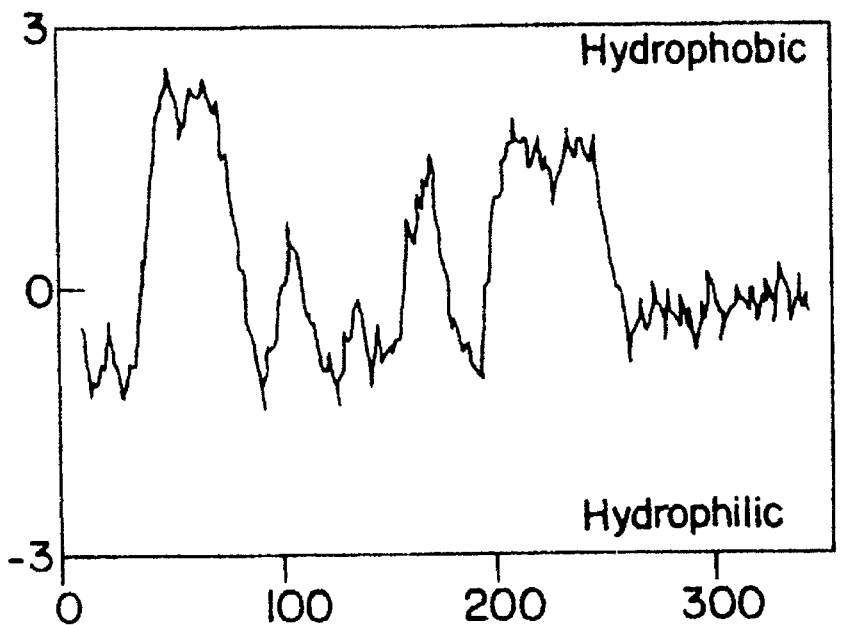
FIG. 1(A and B) depicts the hydropathy profiles of the deduced amino acid sequences of Synechocystis Δ6-desaturase (Panel A) and Δ12-desaturase (Panel B). Putative membrane spanning regions are indicated by solid bars. Hydrophobic index was calculated for a window size of 19 amino acid residues [Kyte, et al. (1982) J. Molec. Biol. 157].

The present invention provides isolated nucleic acids encoding Δ6-desaturase. To identify a nucleic acid encoding Δ6-desaturase, DNA is isolated from an organism which produces GLA. Said organism can be, for example, an animal cell, certain fungi (e.g. Mortierella), certain bacteria (e.g. Synechocystis) or certain plants (borage, Oenothera, currants). The isolation of genomic DNA can be accomplished by a variety of methods well-known to one of ordinary skill in the art, as exemplified by Sambrook et al. (1989) in *Molecular Cloning: A Laboratory Manual*, Cold Spring Harbor, N.Y. The isolated DNA is fragmented by physical methods or enzymatic digestion and cloned into an appropriate vector, e.g. a bacteriophage or cosmid vector, by any of a variety of well-known methods which can be found in references such as Sambrook et al. (1989). Expression vectors containing the DNA of the present invention are specifically contemplated herein. DNA encoding Δ6-desaturase can be identified by gain of function analysis. The vector containing fragmented DNA is transferred, for example by infection, transconjugation, transfection, into a host organism that produces linoleic acid but not GLA. As used herein, "transformation" refers generally to the incorporation of foreign DNA into a host cell. Methods for introducing recombinant DNA into a host organism are known to one of ordinary skill in the art and can be found, for example, in Sambrook et al. (1989). Production of GLA by these organisms (i.e., gain of function) is assayed, for example by gas chromatography or other methods known to the ordinarily skilled artisan. Organisms which are induced to produce GLA, i.e. have gained function by the introduction of the vector, are identified as expressing DNA encoding Δ6-desaturase, and said DNA is recovered from the organisms. The recovered DNA can again be fragmented, cloned with expression vectors, and functionally assessed by the above procedures to define with more particularity the DNA encoding Δ6-desaturase.

As an example of the present invention, random DNA is isolated from the cyanobacteria Synechocystis Pasteur Culture Collection (PCC) 6803, American Type Culture Collection (ATCC) 27184, cloned into a cosmid vector, and introduced by transconjugation into the GLA-deficient cyanobacterium Anabaena strain PCC 7120, ATCC 27893. Production of GLA from Anabaena linoleic acid is monitored by gas chromatography and the corresponding DNA fragment is isolated.

The isolated DNA is sequenced by methods well-known to one of ordinary skill in the art as found, for example, in Sambrook et al. (1989).

In accordance with the present invention, DNA molecules comprising Δ6-desaturase genes have been isolated. More particularly, a 3.588 kilobase (kb) DNA comprising a Δ6-desaturase gene has been isolated from the cyanobacteria Synechocystis. The nucleotide sequence of the 3.588 kb DNA was determined and is shown in SEQ ID NO:1. Open reading frames defining potential coding regions are present from nucleotide 317 to 1507 and from nucleotide 2002 to 3081. To define the nucleotides responsible for encoding Δ6-desaturase, the 3.588 kb fragment that confers Δ6-desaturase activity is cleaved into two subfragments, each of which contains only one open reading frame. Fragment ORF1 contains nucleotides 1 through 1704, while fragment ORF2 contains nucleotides 1705 through 3588. Each fragment is subcloned in both forward and reverse orientations into a conjugal expression vector (AM542, Wolk et al. [1984] *Proc. Natl. Acad. Sci. U.S.A.* 81, 1561) that contains a cyanobacterial carboxylase promoter. The resulting constructs (i.e. ORF1(F), ORF1(R), ORF2(F) and ORF2(R)] are conjugated to wild-type Anabaena PCC 7120 by standard methods (see, for example, Wolk et al. (1984) *Proc. Natl. Acad. Sci. U.S.A.* 81, 1561). Conjugated cells of Anabaena are identified as Neo® green colonies on a brown background of dying non-conjugated cells after two weeks of growth on selective media (standard mineral media BGllN+ containing 30 µg/ml of neomycin according to Rippka et al., (1979) *J. Gen Microbiol.* 111., 1). The green colonies are selected and grown in selective liquid media (BGllN+ with 15 µg/ml neomycin). Lipids are extracted by standard methods (e.g. Dahmer et al., (1989) *Journal of American Oil Chemical Society* 66, 543) from the resulting transconjugants containing the forward and reverse oriented ORF1 and ORF2 constructs. For comparison, lipids are also extracted from wild-type cultures of Anabaena and Synechocystis. The fatty acid methyl esters are analyzed by gas liquid chromatography (GLC), for example with a Tracor-560 gas liquid chromatograph equipped with a hydrogen flame ionization detector and a capillary column. The results of GLC analysis are shown in Table 1.

TABLE 1

Occurrence of C18 fatty acids in wild-type and transgenic cyanobacteria

| SOURCE | 18:0 | 18:1 | 18:2 | γ18:3 | α18:3 | 18:4 |
|---|---|---|---|---|---|---|
| Anabaena (wild type) | + | + | + | − | + | − |
| Anabaena + ORF1(F) | + | + | + | − | + | − |
| Anabaena + ORF1(R) | + | + | + | − | + | − |
| Anabaena + ORF2(F) | + | + | + | + | + | + |
| Anabaena + ORF2(R) | + | + | + | − | + | − |
| Synechocystis (wild type) | + | + | + | + | − | − |

Figure 1B:
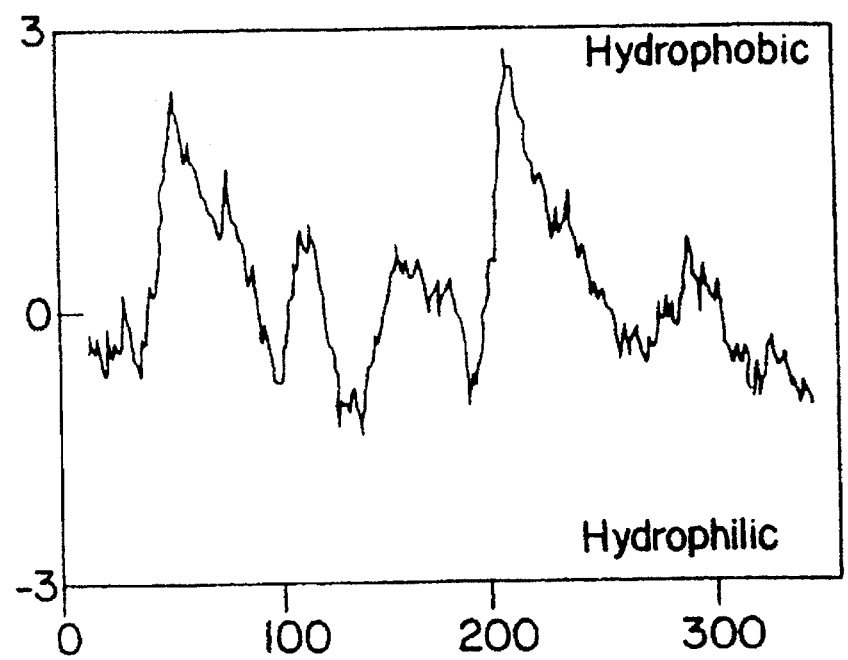

As assessed by GLC analysis, GLA deficient Anabaena gain the function of GLA production when the construct containing ORF2 in forward orientation is introduced by transconjugation. Transconjugants containing constructs with ORF2 in reverse orientation to the carboxylase promoter, or ORF1 in either orientation, show no GLA production. This analysis demonstrates that the single open reading frame (ORF2) within the 1884 bp fragment encodes Δ6-desaturase. The 1884 bp fragment is shown as SEQ ID NO:3. This is substantiated by the overall similarity of the hydropathy profiles between Δ6-desaturase and Δ12-desaturase [Wada et al. (1990) *Nature* 347] as shown in FIG. 1 as (A) and (B), respectively.

Also in accordance with the present invention, a cDNA comprising a Δ6-desaturase gene from borage (*Borago officinalis*) has been isolated. The nucleotide sequence of the 1.685 kilobase (kb) cDNA was determined and is shown in FIG. 5A (SEQ ID NO: 4). The ATG start codon and stop codon are underlined. The amino acid sequence corresponding to the open reading frame in the borage delta 6-desaturase is shown in FIG. 5B (SEQ ID NO: 5).

Isolated nucleic acids encoding Δ6-desaturase can be identified from other GLA-producing organisms by the gain of function analysis described above, or by nucleic acid hybridization techniques using the isolated nucleic acid which encodes Synechocystis or borage Δ6-desaturase as a hybridization probe. Both genomic and cDNA cloning methods are known to the skilled artisan and are contemplated by the present invention. The hybridization probe can comprise the entire DNA sequence disclosed as SEQ. ID NO:1 or SEQ. ID NO:4, or a restriction fragment or other DNA fragment thereof, including an oligonucleotide probe. Methods for cloning homologous genes by cross-hybridization are known to the ordinarily skilled artisan and can be found, for example, in Sambrook (1989) and Beltz et al. (1983) *Methods in Enzymology* 100, 266.

In another method of identifying a delta 6-desaturase gene from an organism producing GLA, a cDNA library is made from poly-A$^+$ RNA isolated from polysomal RNA. In order to eliminate hyper-abundant expressed genes from the cDNA population, cDNAs or fragments thereof corresponding to hyper-abundant cDNAs genes are used as hybridization probes to the cDNA library. Non hybridizing plaques are excised and the resulting bacterial colonies are used to inoculate liquid cultures and sequenced. For example, as a means of eliminating other seed storage protein cDNAs from a cDNA library made from borage polysomal RNA, cDNAs corresponding to abundantly expressed seed storage proteins are first hybridized to the cDNA library. The "subtracted" DNA library is then used to generate expressed sequence tags (ETSs) and such tags are used to scan a data base such as GenBank to identify potential desaturates.

Transgenic organisms which gain the function of GLA production by introduction of DNA encoding Δ-6 desaturase also gain the function of octadecatetraeonic acid (18:4Δ$^{6,9,12,15}$) production. Octadecatetraeonic acid is present normally in fish oils and in some plant species of the Boraginaceae family (Craig et al. [1964] *J. Amer. Oil Chem. Soc.* 41, 209–211; Gross et al. [1976] *Can. J. Plant Sci.* 56, 659–664). In the transgenic organisms of the present invention, octadecatetraenoic acid results from further desaturation of α-linolenic acid by Δ6-desaturase or desaturation of GLA by Δ15-desaturase.

The 359 amino acids encoded by ORF2, i.e. the open reading frame encoding Synechocystis Δ6-desaturase, are shown as SEQ. ID NO:2. The open reading frame encoding the borage Δ6-desaturase is shown in SEQ ID NO: 5. The present invention further contemplates other nucleotide sequences which encode the amino acids of SEQ ID NO:2 and SEQ ID NO: 5. It is within the ken of the ordinarily skilled artisan to identify such sequences which result, for example, from the degeneracy of the genetic code. Furthermore, one of ordinary skill in the art can determine, by the gain of function analysis described hereinabove, smaller subfragments of the fragments containing the open reading frames which encode Δ6-desaturases.

The present invention contemplates any such polypeptide fragment of Δ6-desaturase and the nucleic acids therefor which retain activity for converting LA to GLA.

In another aspect of the present invention, a vector containing a nucleic acid of the present invention or a smaller fragment containing the promoter, coding sequence and termination region of a Δ6-desaturase gene is transferred into an organism, for example, cyanobacteria, in which the Δ6-desaturase promoter and termination regions are functional. Accordingly, organisms producing recombinant Δ6-desaturase are provided by this invention. Yet another aspect of this invention provides isolated Δ6-desaturase, which can be purified from the recombinant organisms by standard methods of protein purification. (For example, see Ausubel et al. [1987] *Current Protocols in Molecular Biology*, Green Publishing Associates, New York).

Vectors containing DNA encoding Δ6-desaturase are also provided by the present invention. It will be apparent to one of ordinary skill in the art that appropriate vectors can be constructed to direct the expression of the Δ6-desaturase coding sequence in a variety of organisms. Replicable expression vectors are particularly preferred. Replicable expression vectors as described herein are DNA or RNA molecules engineered for controlled expression of a desired gene, i.e. the Δ6-desaturase gene. Preferably the vectors are plasmids, bacteriophages, cosmids or viruses. Shuttle vectors, e.g. as described by Wolk et al. (1984) *Proc. Natl. Acad. Sci. U.S.A.*, 1561–1565 and Bustos et al. (1991) *J. Bacteriol.* 174, 7525–7533, are also contemplated in accordance with the present invention. Sambrook et al. (1989), Goeddel, ed. (1990) *Methods in Enzymology* 185 Academic Press, and Perbal (1988) *A Practical Guide to Molecular Cloning*, John Wiley and Sons, Inc., provide detailed reviews of vectors into which a nucleic acid encoding the present Δ6-desaturase can be inserted and expressed. Such vectors also contain nucleic acid sequences which can effect expression of nucleic acids encoding Δ6-desaturase. Sequence elements capable of effecting expression of a gene product include promoters, enhancer elements, upstream activating sequences, transcription termination signals and polyadenylation sites. Both constitutive and tissue specific promoters are contemplated. For transformation of plant cells, the cauliflower mosaic virus (CaMV) 35S promoter and promoters which are regulated during plant seed maturation are of particular interest. All such promoter and transcriptional regulatory elements, singly or in combination, are contemplated for use in the present replicable expression vectors and are known to one of ordinary skill in the art. The CaMV 35S promoter is described, for example, by Restrepo et al. (1990) *Plant Cell* 2, 987. Genetically engineered and mutated regulatory sequences are also contemplated.

The ordinarily skilled artisan can determine vectors and regulatory elements suitable for expression in a particular host cell. For example, a vector comprising the promoter from the gene encoding the carboxylase of Anabaena operably linked to the coding region of Δ6-desaturase and further operably linked to a termination signal from Synechocystis is appropriate for expression of Δ6-desaturase in cyanobacteria. "Operably linked" in this context means that the promoter and terminator sequences effectively function to regulate transcription. As a further example, a vector appropriate for expression of Δ6-desaturase in transgenic plants can comprise a seed-specific promoter sequence derived from helianthinin, napin, or glycinin operably linked to the Δ6-desaturase coding region and further operably linked to a seed termination signal or the nopaline synthase termination signal. As a still further example, a vector for use in expression of Δ6-desaturase in plants can comprise a constitutive promoter or a tissue specific promoter operably linked to the Δ6-desaturase coding region and further operably linked to a constitutive or tissue specific terminator or the nopaline synthase termination signal.

In particular, the helianthinin regulatory elements disclosed in applicant's copending U.S. application Ser. No.

682,354, filed Apr. 8, 1991 and incorporated herein by reference, are contemplated as promoter elements to direct the expression of the Δ6-desaturase of the present invention.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such hybrid vectors are well-known to those of ordinary skill in the art and can be found in references such as Sambrook et al. (1989), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in the hybrid vectors other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985) *Nature* 313, 358. Prokaryotic and eukaryotic signal sequences are disclosed, for example, by Michaelis et al. (1982) *Ann. Rev. Microbiol.* 36, 425.

A further aspect of the instant invention provides organisms other than cyanobacteria or plants which contain the DNA encoding the Δ6-desaturase of the present invention. The transgenic organisms contemplated in accordance with the present invention include bacteria, cyanobacteria, fungi, and plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989).

A variety of plant transformation methods are known. The Δ6-desaturase gene can be introduced into plants by a leaf disk transformation-regeneration procedure as described by Horsch et al. (1985) *Science* 227, 1229. Other methods of transformation, such as protoplast culture (Horsch et al. (1984) *Science* 223, 496; DeBlock et al. (1984) *EMBO J.* 2, 2143; Barton et al. (1983) *Cell* 32, 1033) can also be used and are within the scope of this invention. In a preferred embodiment plants are transformed with Agrobacterium-derived vectors. However, other methods are available to insert the Δ6-desaturase genes of the present invention into plant cells. Such alternative methods include biolistic approaches (Klein et al. (1987) *Nature* 327, 70), electroporation, chemically-induced DNA uptake, and use of viruses or pollen as vectors.

When necessary for the transformation method, the Δ6-desaturase genes of the present invention can be inserted into a plant transformation vector, e.g. the binary vector described by Bevan (1984) *Nucleic Acids Res.* 12, 8111. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

Surface-sterilized leaf disks are inoculated with the "disarmed" foreign DNA-containing *A. tumefaciens*, cultured for two days, and then transferred to antibiotic-containing medium. Transformed shoots are selected after rooting in medium containing the appropriate antibiotic, transferred to soil and regenerated.

Another aspect of the present invention provides transgenic plants or progeny of these plants containing the isolated DNA of the invention. Both monocotyledenous and dicotyledenous plants are contemplated. Plant cells are transformed with the isolated DNA encoding Δ6-desaturase by any of the plant transformation methods described above. The transformed plant cell, usually in a callus culture or leaf disk, is regenerated into a complete transgenic plant by methods well-known to one of ordinary skill in the art (e.g. Horsch et al. (1985) *Science* 227, 1129). In a preferred embodiment, the transgenic plant is sunflower, oil seed rape, maize, tobacco, peanut or soybean. Since progeny of transformed plants inherit the DNA encoding Δ6-desaturase, seeds or cuttings from transformed plants are used to maintain the transgenic plant line.

The present invention further provides a method for providing transgenic plants with an increased content of GLA. This method includes introducing DNA encoding Δ6-desaturase into plant cells which lack or have low levels of GLA but contain LA, and regenerating plants with increased GLA content from the transgenic cells. In particular, commercially grown crop plants are contemplated as the transgenic organism, including, but not limited to, sunflower, soybean, oil seed rape, maize, peanut and tobacco.

The present invention further provides a method for providing transgenic organisms which contain GLA. This method comprises introducing DNA encoding Δ6-desaturase into an organism which lacks or has low levels of GLA, but contains LA. In another embodiment, the method comprises introducing one or more expression vectors which comprise DNA encoding Δ12-desaturase and Δ6-desaturase into organisms which are deficient in both GLA and LA. Accordingly, organisms deficient in both LA and GLA are induced to produce LA by the expression of Δ12-desaturase, and GLA is then generated due to the expression of Δ6-desaturase. Expression vectors comprising DNA encoding Δ12-desaturase, or Δ12-desaturase and Δ6-desaturase, can be constructed by methods of recombinant technology known to one of ordinary skill in the art (Sambrook et al., 1989) and the published sequence of Δ12-desaturase (Wada et al [1990] *Nature (London)* 347, 200–203. In addition, it has been discovered in accordance with the present invention that nucleotides 2002–3081 of SEQ. ID NO:1 encode cyanobacterial Δ12-desaturase. Accordingly, this sequence can be used to construct the subject expression vectors. In particular, commercially grown crop plants are contemplated as the transgenic organism, including, but not limited to, sunflower, soybean, oil seed rape, maize, peanut and tobacco.

The present invention is further directed to a method of inducing chilling tolerance in plants. Chilling sensitivity may be due to phase transition of lipids in cell membranes. Phase transition temperature depends upon the degree of unsaturation of fatty acids in membrane lipids, and thus increasing the degree of unsaturation, for example by introducing Δ6-desaturase to convert LA to GLA, can induce or improve chilling resistance. Accordingly, the present method comprises introducing DNA encoding Δ6-desaturase into a plant cell, and regenerating a plant with improved chilling resistance from said transformed plant cell. In a preferred embodiment, the plant is a sunflower, soybean, oil seed rape, maize, peanut or tobacco plant.

DESCRIPTION OF THE PREFERRED EMBODIMENTS

The following examples further illustrate the present invention.

EXAMPLE 1

Strains and Culture Conditions

Synechocystis (PCC 6803, ATCC 27184), Anabaena (PCC 7120, ATCC 27893) and Synechococcus (PCC 7942, ATCC 33912) were grown photoautotrophically at 30° C. in BG11N+ medium (Rippka et al. [1979] *J. Gen. Microbiol.* 111, 1–61) under illumination of incandescent lamps (60 $\mu E.m^{-2}.S^{-1}$). Cosmids and plasmids were selected and propagated in *Escherichia coli* strain DH5α on LB medium supplemented with antibiotics at standard concentrations as described by Maniatis et al. (1982) *Molecular Cloning: A Laboratory Manual*, Cold Spring Harbor Laboratory, Cold Spring, N.Y.

EXAMPLE 2

Construction of Synechocystis Cosmid Genomic Library

Total genomic DNA from Synechocystis (PCC 6803) was partially digested with Sau3A and fractionated on a sucrose gradient (Ausubel et al. [1987] *Current Protocols in Molecular Biology*, Greene Publishing Associates and Wiley Interscience, New York). Fractions containing 30 to 40 kb DNA fragments were selected and ligated into the dephosphorylated BamHI site of the cosmid vector, pDUCA7 (Buikema et al. [1991] *J. Bacteriol.* 173, 1879–1885). The ligated DNA was packaged in vitro as described by Ausubel et al. (1987), and packaged phage were propagated in *E. coli* DH5α containing the AvaI and Eco4711 methylase helper plasmid, pRL528 as described by Buikema et al. (1991). A total of 1152 colonies were isolated randomly and maintained individually in twelve 96-well microtiter plates.

EXAMPLE 3

Gain-of-Function Expression of GLA in Anabaena

Anabaena (PCC 7120), a filamentous cyanobacterium, is deficient in GLA but contains significant amounts of linoleic acid, the precursor for GLA (FIG. 2; Table 2). The Synechocystis cosmid library described in Example 2 was conjugated into Anabaena (PCC 7120) to identify transconjugants that produce GLA. Anabaena cells were grown to mid-log phase in BG11N+ liquid medium and resuspended in the same medium to a final concentration of approximately $2\times10^8$ cells per ml. A mid-log phase culture of *E. coli* RP4 (Burkardt et al. [1979] *J. Gen. Microbiol.* 14, 341–348) grown in LB containing ampicillin was washed and resuspended in fresh LB medium. Anabaena and RP4 were then mixed and spread evenly on BG11N+ plates containing 5% LB. The cosmid genomic library was replica plated onto LB plates containing 50 µg/ml kanamycin and 17.5 µg/ml chloramphenicol and was subsequently patched onto BG11N+ plates containing Anabaena and RP4. After 24 hours of incubation at 30° C., 30 µg/ml of neomycin was underlaid; and incubation at 30° C. was continued until transconjugants appeared.

Individual transconjugants were isolated after conjugation and grown in 2 ml BG11N+ liquid medium with 15 µg/ml neomycin. Fatty acid methyl esters were prepared from wild type cultures and cultures containing pools of ten transconjugants as follows. Wild type and transgenic cyanobacterial cultures were harvested by centrifugation and washed twice with distilled water. Fatty acid methyl esters were extracted from these cultures as described by Dahmer et al. (1989) *J. Amer. Oil. Chem. Soc.* 66, 543–548 and were analyzed by Gas Liquid Chromatography (GLC) using a Tracor-560 equipped with a hydrogen flame ionization detector and capillary column (30 m×0.25 mm bonded FSOT Superox II, Alltech Associates Inc., Ill.). Retention times and co-chromatography of standards (obtained from Sigma Chemical Co.) were used for identification of fatty acids. The average fatty acid composition was determined as the ratio of peak area of each C18 fatty acid normalized to an internal standard.

Representative GLC profiles are shown in FIG. 2. C18 fatty acid methyl esters are shown. Peaks were identified by comparing the elution times with known standards of fatty acid methyl esters and were confirmed by gas chromatography-mass spectrometry. Panel A depicts GLC analysis of fatty acids of wild type Anabaena. The arrow indicates the migration time of GLA. Panel B is a GLC profile of fatty acids of transconjugants of Anabaena with pAM542+1.8F. Two GLA producing pools (of 25 pools representing 250 transconjugants) were identified that produced GLA. Individual transconjugants of each GLA positive pool were analyzed for GLA production; two independent transconjugants, AS13 and AS75, one from each pool, were identified which expressed significant levels of GLA and which contained cosmids, cSy13 and cSy75, respectively (FIG. 3). The cosmids overlap in a region approximately 7.5 kb in length. A 3.5 kb NheI fragment of cSy75 was recloned in the vector pDUCA7 and transferred to Anabaena resulting in gain-of-function expression of GLA (Table 2).

Two NheI/Hind III subfragments (1.8 and 1.7 kb) of the 3.5 kb Nhe I fragment of cSy75-3.5 were subcloned into "pBLUESCRIPT" (Stratagene) (FIG. 3) for sequencing. Standard molecular biology techniques were performed as described by Maniatis et al. (1982) and Ausubel et al. (1987). Dideoxy sequencing (Sanger et al. [1977] *Proc. Natl. Acad. Sci. U.S.A.* 74, 5463–5467) of pBS1.8 was performed with "SEQUENASE" (United States Biochemical) on both strands by using specific oligonucleotide primers synthesized by the Advanced DNA Technologies Laboratory (Biology Department, Texas A & M University). DNA sequence analysis was done with the GCG (Madison, Wis.) software as described by Devereux et al. (1984) *Nucleic Acids Res.* 12, 387–395.

Both NheI/HindIII subfragments were transferred into a conjugal expression vector, AM542, in both forward and reverse orientations with respect to a cyanobacterial carboxylase promoter and were introduced into Anabaena by conjugation. Transconjugants containing the 1.8 kb fragment in the forward orientation (AM542-1.8F) produced significant quantities of GLA and octadecatetraenoic acid (FIG. 2; Table 2). Transconjugants containing other constructs, either reverse oriented 1.8 kb fragment or forward and reverse oriented 1.7 kb fragment, did not produce detectable levels of GLA (Table 2).

Figure 2A:
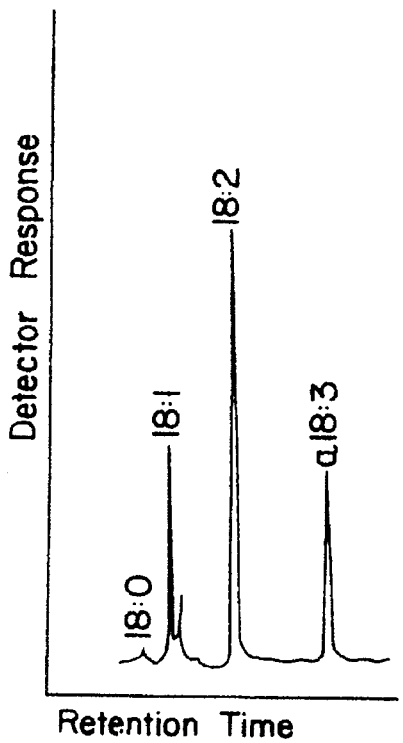
FIG. 2(A and B) provides gas liquid chromatography profiles of wild type (Panel A) and transgenic (Panel B) Anabaena.
Figure 2B:
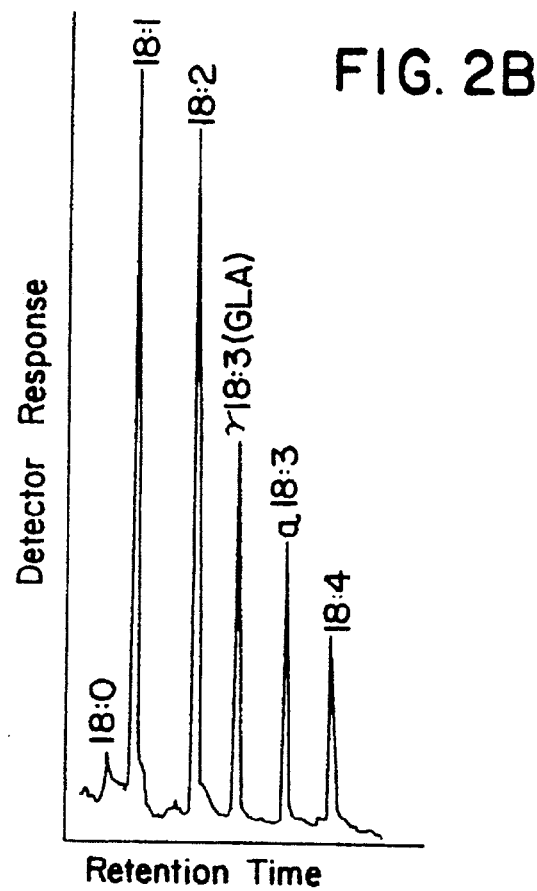
Figure 3:
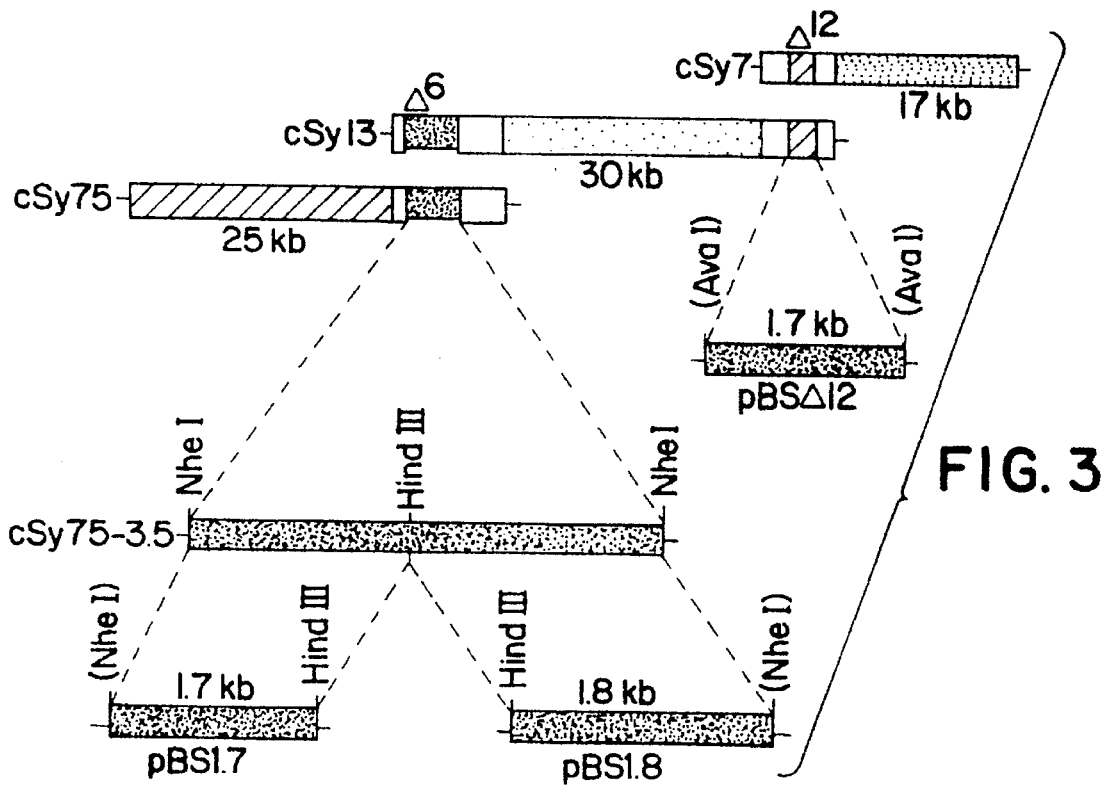
FIG. 3 is a diagram of maps of cosmid cSy75, cSy13 and Csy7 with overlapping regions and subclones. The origins of subclones of Csy75, Csy75-3.5 and Csy7 are indicated by the dashed diagonal lines. Restriction sites that have been inactivated are in parentheses.

FIG. 2 compares the C18 fatty acid profile of an extract from wild type Anabaena (FIG. 2A) with that of transgenic Anabaena containing the 1.8 kb fragment of cSy75-3.5 in the forward orientation (FIG. 2B). GLC analysis of fatty acid methyl esters from AM542-1.8F revealed a peak with a retention time identical to that of authentic GLA standard. Analysis of this peak by gas chromatography-mass spectrometry (GC-MS) confirmed that it had the same mass fragmentation pattern as a GLA reference sample. Transgenic Anabaena with altered levels of polyunsaturated fatty acids were similar to wild type in growth rate and morphology.

TABLE 2

Composition of C18 Fatty Acids in Wild Type and Transgenic Cyanobacteria

| Strain | Fatty acid (%) | | | | | |
|---|---|---|---|---|---|---|
| | 18:0 | 18:1 | 18:2 | 18:3($\alpha$) | 18:3($\gamma$) | 18:4 |
| Wild type | | | | | | |
| Synetocystis (sp. PCC 6803) | 13.6 | 4.5 | 54.5 | — | 27.3 | — |
| Anabaena (sp. PCC7170) | 2.9 | 24.8 | 37.1 | 35.2 | — | — |
| Synechococcus (sp. PCC 7942) | 20.6 | 79.4 | — | — | — | — |
| Anabaena Transconjugants | | | | | | |
| cSy75 | 3.8 | 24.4 | 22.3 | 9.1 | 27.9 | 12.5 |
| cSy75-3.5 | 4.3 | 27.6 | 18.1 | 3.2 | 40.4 | 6.4 |
| pAM542-1.8F | 4.2 | 13.9 | 12.1 | 19.1 | 25.4 | 25.4 |
| pAM542-1.8R | 7.7 | 23.1 | 38.4 | 30.8 | — | — |
| pAM542-1.7F | 2.8 | 27.8 | 36.1 | 33.3 | — | — |
| pAM542-1.7R | 2.8 | 25.4 | 42.3 | 29.6 | — | — |
| Synechococcus Transformants | | | | | | |
| pAM854 | 27.8 | 72.2 | — | — | — | — |
| pAM854-$\Delta^{12}$ | 4.0 | 43.2 | 46.0 | — | — | — |
| pAM854-$\Delta^{6}$ | 18.2 | 81.8 | — | — | — | — |
| pAM854-$\Delta^{6}$ & $\Delta^{12}$ | 42.7 | 25.3 | 19.5 | — | 16.5 | — |

18:0, stearic acid; 18:1, oleic acid; 18:2, linoleic acid; 18:3($\alpha$), $\alpha$-linolenic acid; 18:3($\gamma$), $\gamma$-linolenic acid; 18:4, octadecatetraenoic acid

EXAMPLE 4

Transformation of Synechococcus with $\Delta 6$ and $\Delta 12$ Desaturase Genes A third cosmid, cSy7, which contains a $\Delta 12$-desaturase gene, was isolated by screening the Synechocystis genomic library with a oligonucleotide synthesized from the published Synechocystis $\Delta 12$-desaturase gene sequence (Wada et al. [1990] *Nature (London)* 347, 200–203). A 1.7 kb AvaI fragment from this cosmid containing the $\Delta 12$-desaturase gene was identified and used as a probe to demonstrate that cSy13 not only contains a $\Delta 6$-desaturase gene but also a $\Delta 12$-desaturase gene (FIG. 3). Genomic Southern blot analysis further showed that both the $\Delta 6$- and $\Delta 12$-desaturase genes are unique in the Synechocystis genome so that both functional genes involved in C18 fatty acid desaturation are linked closely in the Synechocystis genome.

The unicellular cyanobacterium Synechococcus (PCC 7942) is deficient in both linoleic acid and GLA(3). The $\Delta 12$ and $\Delta 6$-desaturase genes were cloned individually and together into pAM854 (Bustos et al. [1991] *J. Bacteriol.* 174, 7525–7533), a shuttle vector that contains sequences necessary for the integration of foreign DNA into the genome of Synechococcus (Golden et al. [1987] *Methods in Enzymol.* 153, 215–231). Synechococcus was transformed with these gene constructs and colonies were selected. Fatty acid methyl esters were extracted from transgenic Synechococcus and analyzed by GLC.

Table 2 shows that the principal fatty acids of wild type Synechococcus are stearic acid (18:0) and oleic acid (18:1). Synechococcus transformed with pAM854-$\Delta 12$ expressed linoleic acid (18:2) in addition to the principal fatty acids. Transformants with pAM854-$\Delta 6$ and $\Delta 12$ produced both linoleate and GLA (Table 1). These results indicated that Synechococcus containing both $\Delta 12$- and $\Delta 6$-desaturase genes has gained the capability of introducing a second double bond at the $\Delta 12$ position and a third double bond at the $\Delta 6$ position of C18 fatty acids. However, no changes in fatty acid composition was observed in the transformant containing pAM854-$\Delta 6$, indicating that in the absence of substrate synthesized by the $\Delta 12$ desaturase, the $\Delta 6$-desaturase is inactive. This experiment further confirms that the 1.8 kb NheI/HindIII fragment (FIG. 3) contains both coding and promoter regions of the Synechocystis $\Delta 6$-desaturase gene. Transgenic Synechococcus with altered levels of polyunsaturated fatty acids were similar to wild type in growth rate and morphology.

EXAMPLE 5

Nucleotide Sequence of $\Delta 6$-Desaturase

Figure 4A:
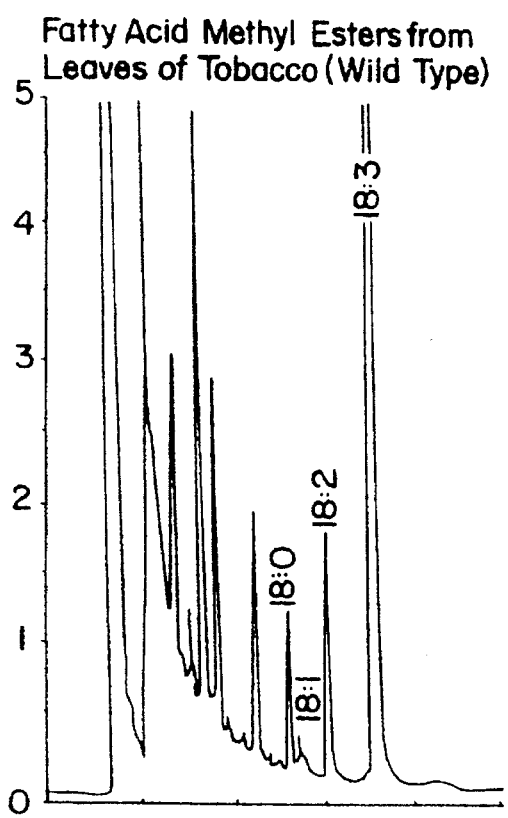
FIG. 4(A and B) provides gas liquid chromatography profiles of wild type (Panel A) and transgenic (Panel B) tobacco.
Figure 4B:
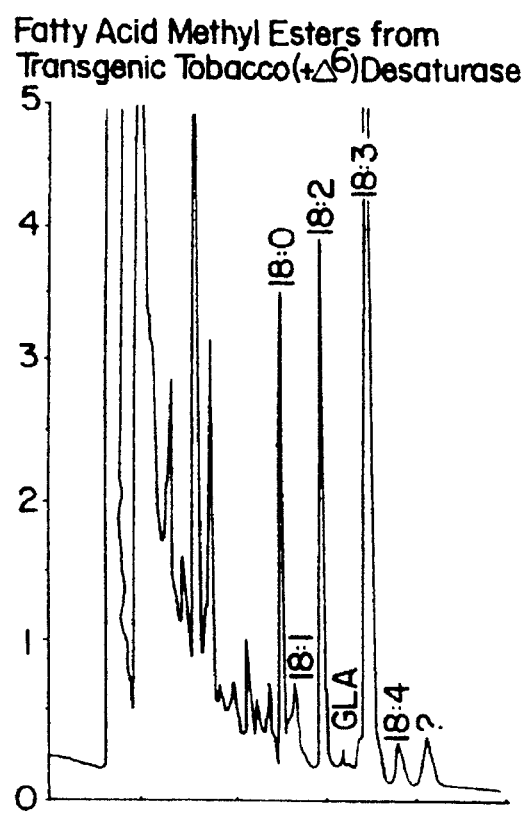

The nucleotide sequence of the 1.8 kb fragment of cSy75-3.5 including the functional $\Delta 6$-desaturase gene was determined. An open reading frame encoding a polypeptide of 359 amino acids was identified (FIG. 4). A Kyte-Doolittle hydropathy analysis (Kyte et al. [1982] *J. Mol. Biol.* 157, 105–132) identified two regions of hydrophobic amino acids that could represent transmembrane domains (FIG. 1A); furthermore, the hydropathic profile of the $\Delta 6$-desaturase is similar to that of the $\Delta 12$-desaturase gene (FIG. 1B; Wada et al.) and $\Delta 9$-desaturases (Thiede et al. [1986] *J. Biol. Chem.* 261, 13230–13235). However, the sequence similarity between the Synechocystis $\Delta 6$- and $\Delta 12$-desaturases is less than 40% at the nucleotide level and approximately 18% at the amino acid level.

EXAMPLE 6

Transfer of Cyanobacterial $\Delta^6$-Desaturase into Tobacco

The cyanobacterial $\Delta^6$-desaturase gene was mobilized into a plant expression vector and transferred to tobacco using Agrobacterium mediated gene transfer techniques. To ensure that the transferred desaturase is appropriately expressed in leaves and developing seeds and that the desaturase gene product is targeted to the endoplasmic reticulum or the chloroplast, various expression cassettes with Synechocystis $\Delta$-desaturase open reading frame (ORF) were constructed. Components of these cassettes include: (i) a 35S promoter or seed specific promoter derived from the sunflower helianthinin gene to drive $\Delta^6$-desaturase gene expression in all plant tissues or only in developing seeds respectively, (ii) a putative signal peptide either from carrot extension gene or sunflower helianthinin gene to target newly synthesized $\Delta^6$-desaturase into the ER, (iii) an ER lumen retention signal sequence (KDEL) at the COOH-terminal of the $\Delta^6$-desaturase ORF, and (iv) an optimized transit peptide to target $\Delta^6$ desaturase into the chloroplast. The 35S promoter is a derivative of pRTL2 described by Restrepo et al. (1990). The optimized transit peptide sequence is described by Van de Broeck et al. (1985). The carrot extension signal peptide is described by Chen et al (1985) *EMBO J.* 9, 2145.

Transgenic tobacco plants were produced containing a chimeric cyanobacterial desaturase gene, comprised of the Synechocystis $\Delta^6$ desaturase gene fused to an endoplasmic reticulum retention sequence (KDEL) and extension signal peptide driven by the CaMV 35S promoter. PCR amplifications of transgenic tobacco genomic DNA indicate that the $\Delta^6$ desaturase gene was incorporated into the tobacco genome. Fatty acid methyl esters of leaves of these transgenic tobacco plants were extracted and analyzed by Gas Liquid Chromatography (GLC). These transgenic tobacco accumulated significant amounts of GLA (FIG. 4). FIG. 4 shows fatty acid methyl esters as determined by GLC. Peaks were identified by comparing the elution times with known standards of fatty acid methyl ester. Accordingly, cyanobacterial genes involved in fatty acid metabolism can be used to generate transgenic plants with altered fatty acid compositions.

EXAMPLE 7

Construction of Borage cDNA Library

Membrane bound polysomes were isolated from borage seeds 12 days post pollination (12 DPP) using the protocol established for peas by Larkins and Davies (1975 *Plant Phys.* 55:749–756). RNA was extracted from the polysomes as described by Mechler (1987 Methods in Enzymology 152:241–248, Academic Press).

Poly-A+ RNA was isolated from the membrane bound polysomal RNA by use of Oligotex-dT beads (Qiagen). Corresponding cDNA was made using Stratagene's ZAP cDNA synthesis kit. The cDNA library was constructed in the lambda ZAP II vector (Stratagene) using the lambda ZAP II vector kit. The primary library was packaged in Gigapack II Gold packaging extract (Stratagene). The library was used to generate expressed sequence tags (ESTs), and sequences corresponding to the tags were used to scan the GenBank database.

EXAMPLE 8

Hybridization Protocol

Hybridization probes for screening the borage cDNA library were generated by using random primed DNA synthesis as described by Ausubel et al (1994 *Current Protocols in Molecular Biology*, Wiley Interscience, New York) and corresponded to previously identified abundantly expressed seed storage protein cDNAs. Unincorporated nucleotides were removed by use of a G-50 spin column (Boehringer Manheim). Probe was denatured for hybridization by boiling in a water bath for 5 minutes, then quickly cooled on ice. Filters for hybridization were prehybridized at 60° C. for 2–4 hours in prehybridization solution (6XSSC [Maniatis et al 1984 Molecular Cloning A Laboratory Manual, Cold Spring Harbor Laboratory], 1X Denharts Solution, 0.05% sodium pyrophosphate, 100 µg/ml denatured salmon sperm DNA). Denatured probe was added to the hybridization solution (6X SSC, 1X Denharts solution, 0.05% sodium pyrophosphate, 100 µg/ml denatured salmon sperm DNA) and incubated at 60° C. with agitation overnight. Filters were washed in 4x, 2x, and 1x SET washes for 15 minutes each at 60° C. A 20X SET stock solution is 3M NaCl, 0.4 M Tris base, 20 mM $Na_2EDTA$-$2H_2O$. The 4X SET wash was 4X SET, 12.5 mM $PO_4$, pH 6.8 and 0.2% SDS. The 2X SET wash was 2X SET, 12.5 mM $PO_4$, pH 6.8 and 0.2% SDS. The 1X SET wash was 1X SET, 12.5 mM $PO_4$, pH 6.8 and 0.2% SDS. Filters were allowed to air dry and were then exposed to X-ray film for 24 hours with intensifying screens at –80° C.

EXAMPLE 9

Random Sequencing of cDNAs from a Borage Seed (12 DPP) Membrane-bound Polysomal Library The borage cDNA library was plated at low density (500 pfu on 150 mm petri dishes). Highly prevalent seed storage protein cDNAs were "subtracted" by screening with the previously identified corresponding cDNAs. Non-hybridizing plaques were excised using Stratagene's excision protocol and reagents. Resulting bacterial colonies were used to inoculate liquid cultures and were either sequenced manually or by an ABI automated sequencer. Each cDNA was sequenced once and a sequence tag generated from 200–300 base pairs. All sequencing was performed by cycle sequencing (Epicentre). Over 300 ESTs were generated. Each sequence tag was compared to GenBank database by BLASTX computer program and a number of lipid metabolism genes, including the $\Delta$6-desaturase were identified.

Database searches with a cDNA clone designated mbp-65 using BLASTX with the GenBank database resulted in a significant match to the Synechocystis $\Delta$6-desaturase. It was determined however, that this clone was not a full length cDNA. A full length cDNA was isolated using mbp-65 to screen the borage membrane-bound polysomal library. The sequence of the isolated cDNA was determined (FIG. 5A, SEQ ID NO:4) and the protein sequence of the open reading frame (FIG. 5B, SEQ ID NO:5) was compared to other known desaturases using Geneworks (IntelliGenetics) protein alignment program (FIG. 2). This alignment indicated that the cDNA was the borage $\Delta$6-desaturase gene.

Figure 6:
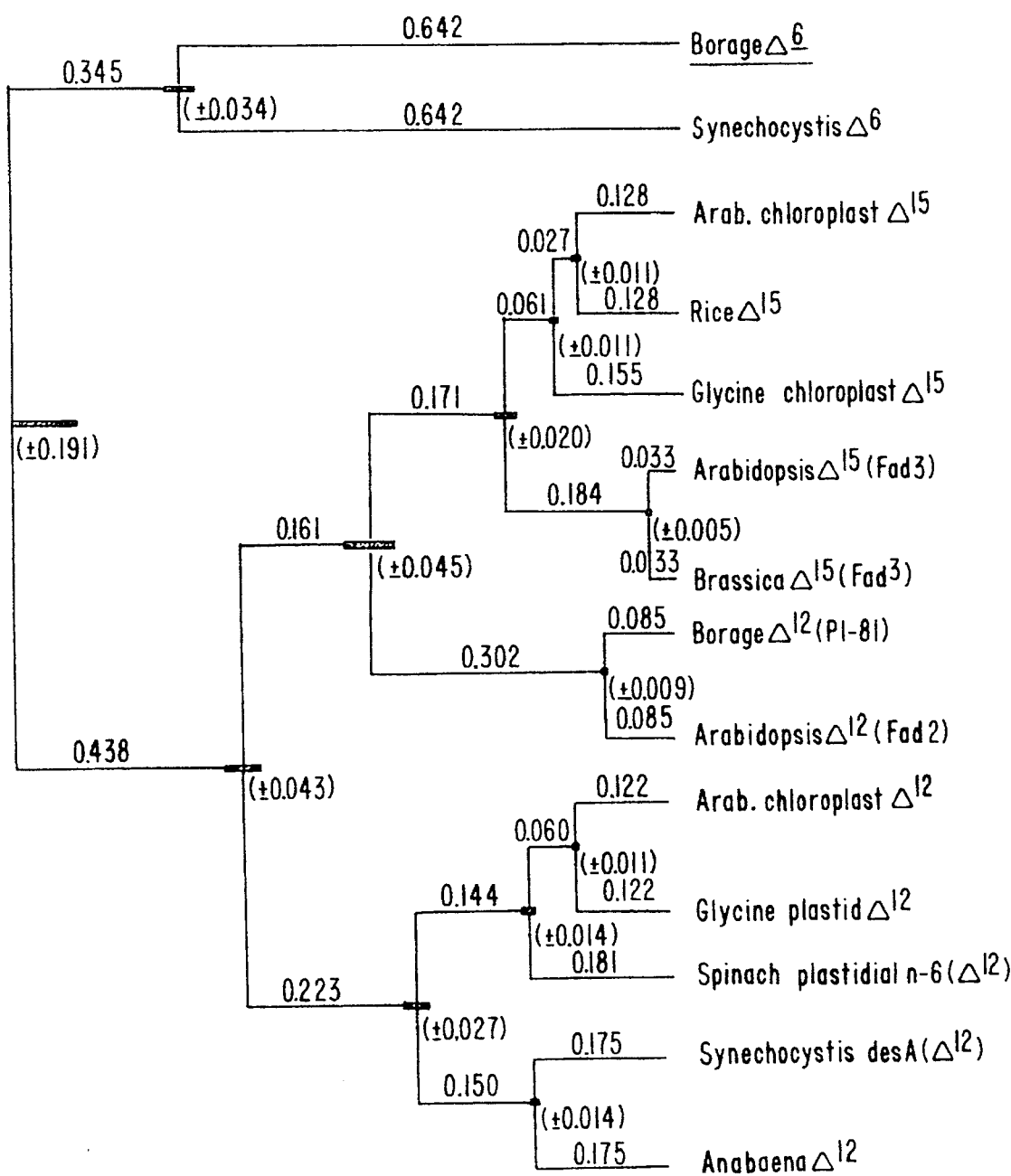
FIG. 6 is a dendrogram showing similarity of the borage Δ6-desaturase to other membrane-bound desaturases. The amino acid sequence of the borage Δ6-desaturase was compared to other known desaturases using Gene Works (IntelliGenetics). Numerical values correlate to relative phylogenetic distances between subgroups compared.

Although similar to other known plant desaturases, the borage delta 6-desaturase is distinct as indicated in the dendrogram shown in FIG. 6. Furthermore, comparison of the amino acid sequences characteristic of desaturases, particularly those proposed to be involved in metal binding (metal box 1 and metal box 2), illustrates the differences between the borage delta 6-desaturase and other plant desaturases (Table 3).

The borage delta 6-desaturase is distinguished from the cyanobacterial form not only in over all sequence (FIG. 6) but also in the lipid box, metal box 1 and metal box 2 amino acid motifs (Table 3). As Table 3 indicates, all three motifs are novel in sequence. Only the borage delta 6-desaturase metal box 2 shown some relationship to the Synechocystis delta-6 desaturase metal box 2.

In addition, the borage delta 6-desaturase is also distinct from another borage desaturase gene, the delta-12 desaturase. P1-81 is a full length cDNA that was identified by EST analysis and shows high similarity to the Arabidopsis delta- 12 desaturase (Fad 2). A comparison of the lipid box, metal box 1 and metal box 2 amino acid motifs (Table 3) in borage delta 6 and delta-12 desaturases indicates that little homology exists in these regions. The placement of the two sequences in the dendrogram in FIG. 6 indicates how distantly related these two genes are.

TABLE 3

Comparison of common amino acid motifs in membrane-bound desaturases

| Desaturase | Amino Acid Motif | | |
|---|---|---|---|
| | Lipid Box | Metal Box 1 | Metal Box 2 |
| Borage $\Delta^6$ | WIGHDAGH (SEQ. ID. NO: 6) | HNAHH (SEQ. ID. NO: 12) | FQUEHH (SEQ. ID. NO: 20) |
| Synechocystis $\Delta^6$ | NVGHDANH (SEQ. ID. NO: 7) | HNYLHH (SEQ. ID. NO: 13) | HQVTHH (SEQ. ID. NO. 21) |
| Arab. chloroplast $\Delta^{15}$ | VLGHDCGH (SEQ. ID. NO: 8) | HRTHH (SEQ. ID. NO: 14) | HVIHH (SEQ. ID. NO. 22) |
| Rice $\Delta^{15}$ | VLHGDCGH (SEQ. ID. NO. 8) | HRTHH (SEQ. ID. NO: 14) | HVIHH (SEQ. ID. NO: 22) |
| Glycine chloroplast $\Delta^{15}$ | VLHGDCHG (SEQ. ID. NO: 8) | HRTHH (SEQ. ID. NO: 14) | HVIHH (SEQ. ID. NO: 22) |
| Arab. fad3 ($\Delta^{15}$) | VLGHDCGH (SEQ. ID. NO: 8) | HRTHH (SEQ. ID. NO: 14) | HVIHH (SEQ. ID. NO: 22) |
| Brassica fad3 ($\Delta^{15}$) | VLGHDCGH (SEQ. ID. NO: 8) | HRTHH (SEQ. ID. NO: 14) | HVIHH (SEQ. ID. NO: 22) |
| Borage $\Delta^{12}$ (P1-81)* | VIAHECGH (SEQ. ID. NO: 9) | HRRHH (SEQ. ID. NO: 15) | HVAHH (SEQ. ID. NO: 23) |
| Arab. fad2 ($\Delta^{12}$) | VIAHECGH (SEQ. ID. NO: 9) | HRRHH (SEQ. ID. NO: 15) | HVAHH (SEQ. ID. NO: 23) |
| Glycine plastid $\Delta^{12}$ | VIGHDCAH (SEQ. ID. NO: 10) | HDRHH (SEQ. ID. NO: 16) | HIPHH (SEQ. ID. NO: 25) |
| Spinach plastidial n-6 | VIGHDCAH (SEQ. ID. NO: 10) | HDRHH (SEQ. ID. NO: 16) | HIPHH (SEQ. ID. NO: 24) |
| Arab. chloroplast $\Delta^{12}$ | VIGHDCAH (SEQ. ID. NO: 10) | HDQHH (SEQ. ID. NO: 17) | HIPHH (SEQ. ID. NO: 24) |
| Synechocystis $\Delta^{12}$ | VVGHDCGH (SEQ. ID. NO: 11) | HDHHH (SEQ. ID. NO: 18) | HIPHH (SEQ. ID. NO: 24) |
| Anabaena $\Delta^{12}$ | VLGHDCGH (SEQ. ID. NO: 8) | HNHHH (SEQ. ID. NO: 19) | HVPHH (SEQ. ID. NO: 25) |

*P1-81 is a full length cDNA which was identified by EST analysis and shows high similarity to the Arbidopsis Δ12 desaturase (fad2)

EXAMPLE 10

Construction of 222.1Δ⁶NOS for Transient and Expression

Figure 7:
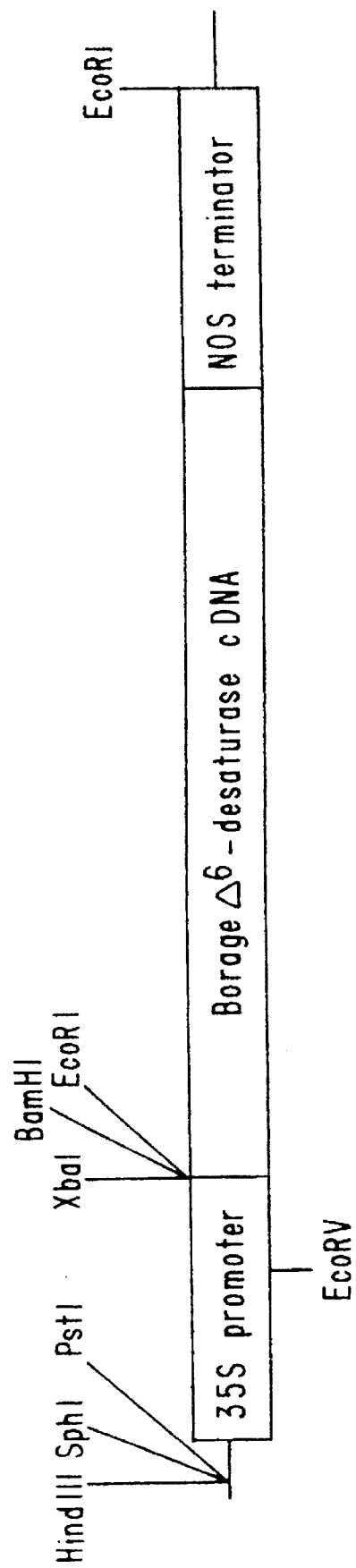
FIG. 7 is a restriction map of 221.Δ6.NOS and 121.Δ6.NOS. In 221.Δ6.NOS, the remaining portion of the plasmid is pBI221 and in 121.Δ6.NOS, the remaining portion of the plasmid is pBI121.

The vector pBI221 (Jefferson et al. 1987 EMBO J. 6:3901–3907) was prepared for ligation by digestion with BamHI and EcoICR I (Promega) which excises the GUS coding region leaving the 35S promoter and NOS terminator intact. The borage Δ6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI221, yielding 221.Δ⁶NOS (FIG. 7). In 222.1Δ⁶.NOS, the remaining portion (backbone) of the restriction map depicted in FIG. 7 is pBI221.

EXAMPLE 11

Construction of 121.Δ⁶.NOS for Stable Transformation

The vector pBI121 (Jefferson et al. 1987 EMBO J. 6:3901–3907) was prepared for ligation by digestion with BamHI and EcoICR I (Promega) which excises the GUS coding region leaving the 35S promoter and NOS terminator intact. The borage Δ6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI121, yielding 121.1Δ⁶NOS (FIG. 7). In 121.1Δ⁶.NOS, the remaining portion (backbone) of the restriction map depicted in FIG. 7 is pBI121.

EXAMPLE 12

Transient Expression

All work involving protoplasts was performed in a sterile hood. One ml of packed carrot suspension cells were digested in 30 mls plasmolyzing solution (25 g/l KCl, 3.5 g/l CaCl$_2$—H$_2$O, 10 mM MES, pH 5.6 and 0.2M mannitol) with 1% cellulase, 0.1% pectolyase, and 0.1% dreisalase overnight, in the dark, at room temperature. Released protoplasts were filtered through a 150 μm mesh and pelleted by centrifugation (100x g, 5 min.) then washed twice in plasmolyzing solution. Protoplasts were counted using a double chambered hemocytometer. DNA was transfected into the protoplasts by PEG treatment as described by Nunberg and Thomas (1993 *Methods in Plant Molecular Biology and Biotechnology*, B. R. Glick and J. E. Thompson, eds. pp. 241–248) using 10⁶ protoplasts and 50–70 ug of plasmid DNA (221.Δ6.NOS). Protoplasts were cultured in 5 mls of MS media supplemented with 0.2M mannitol and 3 μm 2,4-D for 48 hours in the dark with shaking.

EXAMPLE 13

Stable Transformation of Tobacco

121.Δ⁶.NOS plasmid construction was used to transform tobacco (Nicotiana tabacum cv. xanthi) via Agrobacterium according to standard procedures (Horsh et al., 1985 Science 227: 1229–1231; Bogue et al., 1990 Mol. Gen. Genet. 221:49–57), except that initial transformants were selected on 100 ug/ml kanamycin.

EXAMPLE 14

Preparation and Analysis of Fatty Acid Methyl Esters (FAMEs)

Tissue from transfected protoplasts and transformed tobacco plants was frozen in liquid nitrogen and lyophilized overnight. FAMEs were prepared as described by Dahmer et al (1989 J. Amer. Oil Chem. Soc. 66:543–548). In some cases, the solvent was evaporated again, and the FAMEs were resuspended in ethyl acetate and extracted once with deionized water to remove any water soluble contaminants. The FAMEs were analyzed by gas chromatography (GC) on a J&W Scientific DB-wax column (30 m length, 0.25 mm ID, 0.25 um film).

Figure 8A:
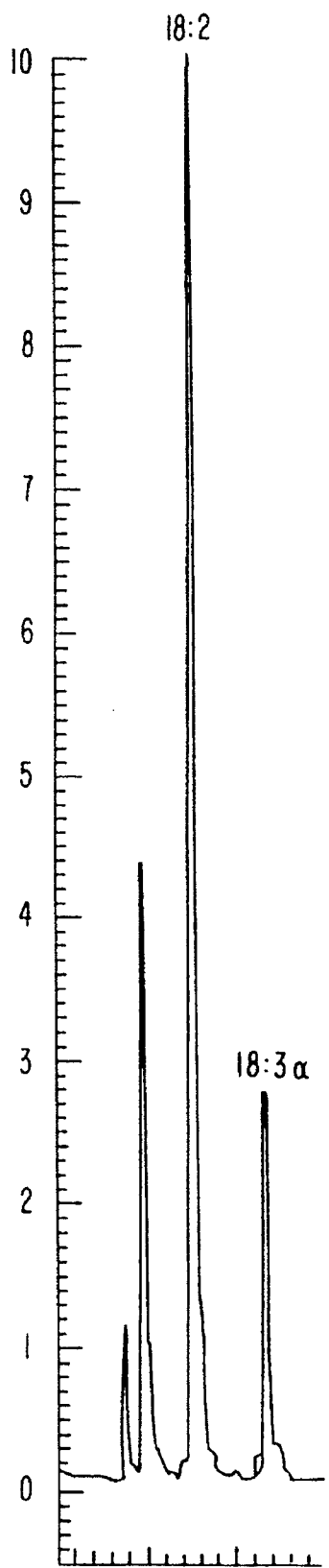
FIG. 8(A and B) provides gas liquid chromatography profiles of mock transfected (Panel A) and 221.Δ6.NOS transfected (Panel B) carrot cells. The positions of 18:2, 18:3 α, and 18:3 γ(GLA) are indicated.
Figure 8B:
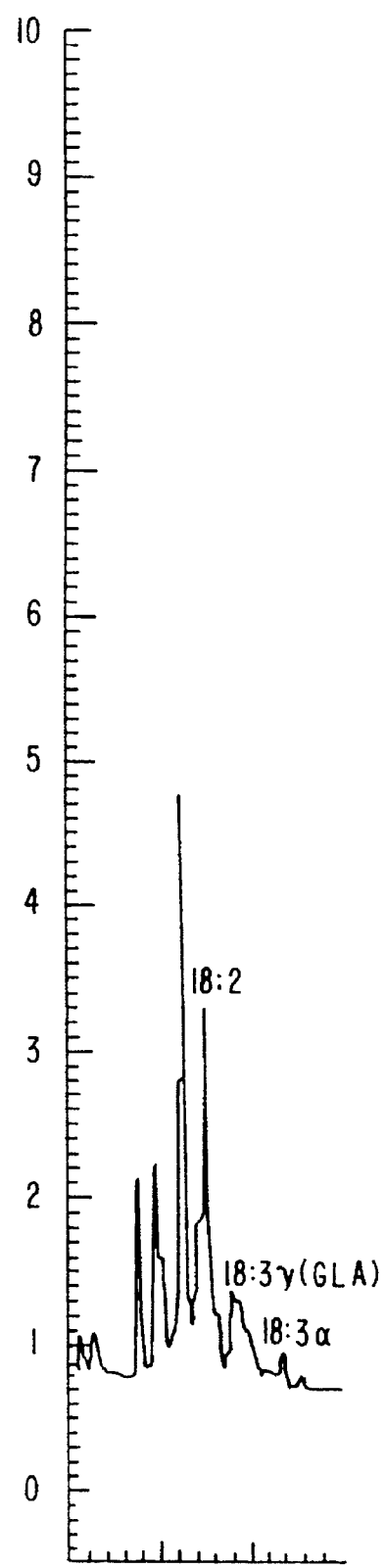

An example of a transient assay is shown in FIG. 8 which represents three independent transfections pooled together. The addition of the borage Δ6-desaturase cDNA corresponds with the appearance of gamma linolenic acid (GLA) which is one of the possible products of Δ6-desaturase. Furthermore, transgenic tobacco containing the borage Δ6-desaturase driven by the cauliflower mosaic virus 35S promoter also produce GLA as well as octa-decaenoic acid (18:4) which is formed by the further desaturation of GLA (FIG. 9).

These results indicate that the borage delta 6-desaturase gene can be used to transform plant cells to achieve altered fatty acid compositions.

What is claimed:

1. An isolated nucleic acid encoding a borage Δ6-desaturase.

2. The isolated nucleic acid of claim 1 comprising the nucleotide sequence of SEQ ID NO: 4.

3. An isolated nucleic acid that codes for the amino acid sequence of SEQ ID NO: 5.

4. A vector comprising the nucleic acid of any one claims 1–3.

5. An expression vector comprising the isolated nucleic acid of any one of claims 1–3 operably linked to a promotor which effects expression of the gene product of said isolated nucleic acid.

6. An expression vector comprising the isolated nucleic acid of any one of claims 1–3 operably linked to a promoter and a termination signal which effects expression of the gene product of said isolated nucleic acid.

7. The expression vector of claim 5 wherein said promoter is a Δ6-desaturase promoter, an Anabaena carboxylase promoter, a helianthinin promoter, a glycinin promoter, a napin promoter, the 35S promoter from CaMV, or a helianthinin tissue-specific promoter.

8. The expression vector of claim 6 wherein said promoter is a Δ-6 desaturase promoter, an Anabaena carboxylase promoter, a helianthinin promoter, a glycinin promoter, a napin promoter, the 35S promoter from CaMV, a helianthinin tissue-specific promoter.

9. An expression vector comprising the isolated nucleic acid of any one of claims 1–3 operably linked to a consitutive promoter.

10. An expression vector comprising the isolated nucleic acid of any one of claims 1–3 operably linked to a tissue specific promoter.

11. The expression vector of claim 6 wherein said termination signal is a Synechocystis termination signal, a nopaline synthase termination signal, or a seed termination signal.

12. A cell comprising the vector of claim 4.
13. A cell comprising the vector of claim 5.
14. A cell comprising the vector of claim 6.

15. The cell of claim 12 wherein said cell is an animal cell, a bacterial cell, a plant cell or a fungal cell.

16. The cell of claim 13 wherein said cell is an animal cell, a bacterial cell, a plant cell or a fungal cell.

17. The cell of claim 14 wherein said cell is an animal cell, a bacterial cell, a plant cell or a fungal cell.

18. A transgenic bacterium or plant comprising the isolated nucleic acid of any one of claims 1–3.

19. A transgenic bacterium or plant comprising the vector of claim 4.

20. A transgenic bacterium or plant comprising the vector of claim 5.

21. A transgenic bacterium or plant comprising the vector of claim 6.

22. A plant or progeny of said plant which has been regenerated from the plant cell of claim 15.

23. The plant of claim 22 wherein said plant is a sunflower, soybean, maize, tobacco, peanut, carrot or oil seed rape plant.

24. A method of producing a plant with increased gamma linolenic acid (GLA) content which comprises:

(a) transforming a plant cell with the isolated nucleic acid of any one of claims 1–3; and
   (b) regenerating a plant with increased GLA content from said plant cell.

25. A method of producing a plant with increased gamma linolenic acid (GLA) content which comprises:

(a) transforming a plant cell with the vector of claim 4; and
   (b) regenerating a plant with increased GLA content from said plant cell.

26. A method of producing a plant with increased gamma linolenic acid (GLA) content which comprises:

(a) transforming a plant cell with the vector of claim 5; and
   (b) regenerating a plant with increased GLA content from said plant cell.

27. A method of producing a plant with increased gamma linolenic acid (GLA) content which comprises:

(a) transforming a plant cell with the vector of claim 6; and (b) regenerating a plant with increased GLA content from said plant cell.

28. The method of claim 24 wherein said plant is a sunflower, soybean, maize, tobacco, peanut, carrot or oil seed rape plant.

29. The method of claim 25 wherein said plant is a sunflower, soybean, maize, tobacco, peanut, carrot or oil seed rape plant.

30. The method of claim 26 wherein said plant is a sunflower, soybean, maize, tobacco, peanut, carrot or oil seed rape plant.

31. The method of claim 27 wherein said plant is a sunflower, soybean, maize, tobacco, peanut, carrot or oil seed rape plant.

32. A method of inducing or increasing production of gamma linolenic acid (GLA) in a bacterium or plant deficient or lacking in or producing low levels Of GLA which comprises transforming said organism with the isolated nucleic acid of any one of claims 1–3.

33. A method of inducing or increasing production of gamma linolenic acid (GLA) in a bacterium or plant deficient or lacking in or producing low levels of GLA which comprises transforming said organism with the vector of claim 4.

34. A method of inducing or increasing production of gamma linolenic acid (GLA) in a bacterium or plant deficient or lacking in or producing low levels of GLA which comprises transforming said organism with the vector of claim 5.

35. A method of inducing or increasing production of gamma linolenic acid (GLA) in a bacterium or plant deficient or lacking in or producing low levels of GLA which comprises transforming said organism with the vector of claim 6.

36. A method of inducing or increasing production of gama linolenic acid (GLA) in a bacterium or plant deficient or lacking in or producing low levels of GLA and linoleic acid (LA) which comprises transforming said organism with an isolated nucleic acid encoding borage $\Delta 6$-desaturase and an isolated nucleic acid encoding $\Delta 12$-desaturase.

37. A method of inducing or increasing production of gamma linolenic acid (GLA) in a bacterium or plant deficient or lacking in or producing low levels of GLA and linoleic acid (LA) which comprises transforming said organism with at least one expression vector comprising an isolated nucleic acid encoding borage $\Delta 6$-desaturase and an isolated nucleic acid encoding $\Delta 12$-desaturase.

38. The method of any one of claims 36 or 37 wherein said isolated nucleic acid encoding $\Delta 6$-desaturase comprises nucleotides 44 to 1390 of SEQ. ID NO: 4.

39. The method of inducing or increasing production of octadecatetraenoic acid in at least one of a plant deficient or lacking in or producing low levels of octadecatetraenoic acid, a bacterium which produces $\alpha$-linolenic acid, or a bacterium which exhibits a $\Delta$-15 desaturase activity on a GLA substrate which comprises transforming said plant or bacterium with the isolated nucleic acid of any one of claims 1–3.

40. The method of inducing or increasing production of octadecatetraenoic acid in at least one of a plant deficient or lacking in or producing low levels of octadecatetraenoic acid, a bacterium which produces $\alpha$-linolenic acid, or a bacterium which exhibits a $\Delta$-15 desaturase activity on a GLA substrate which comprises transforming said plant or bacterium with the vector of claim 4.

41. The method of inducing or increasing production of octadecatetraenoic acid in at least one of a plant deficient or lacking in or producing low levels of octadecatetraenoic acid, a bacterium which produces $\alpha$-linolenic acid, or a bacterium which exhibits a $\Delta$-15 desaturase activity on a GLA substrate which comprises transforming said plant or bacterium with the vector of claim 5.

42. The method of inducing or increasing production of octadecatetraenoic acid in at least one of a plant deficient or lacking in or producing low levels of octadecatetraenoic acid, a bacterium which produces $\alpha$-linolenic acid, or a bacterium which exhibits a $\Delta$-15 desaturase activity on a GLA substrate which comprises transforming said plant or bacterium with the vector of claim 6.

43. The method of inducing or increasing production of octadecatetraenoic acid in at least one of a plant deficient or lacking in or producing low levels of octadecatetraeonic acid, a bacterium which produces $\alpha$-linolenic acid, or a bacterium which exhibits a $\Delta$-15 desaturase activity on a GLA substrate which comprises transforming said plant or bacterium with the vector of claim 7.

44. The method of claim 42 wherein said plant is a sunflower, soybean, maize, tobacco, peanut, carrot or oil seed rape plant.

* * * * *

UNITED STATES PATENT AND TRADEMARK OFFICE
CERTIFICATE OF CORRECTION

PATENT NO. : 5,614,393

DATED : March 25, 1997

INVENTOR(S) : Terry Thomas, et al.

It is certified that error appears in the above-identified patent and that said Letters Patent is hereby corrected as shown below:

On the Title Page, Section [56], under "OTHER PUBLICATIONS--, line 4: --Jun. 16-- should read -- Jun. 26--

Column 5, line 39: -- $\binom{12,15}{}$ )-- should read -- $\binom{12,15}{}$ )--

Column 9, line 66: --14,-- should read --114,--

Column 15, line 17: --VLHGDCGH-- should read --VLGHDCGH--

Column 15, line 18: --VLHGDCHG-- should read --VLGHDCGH--

Column 15, line 23: --HIPHH (SEQ. ID. NO: 25)" should read --HIPHH (SEQ. ID. NO: 24)--

Signed and Sealed this

Twenty-fifth Day of January, 2000

Attest:

Attesting Officer

*Acting Commissioner of Patents and Trademarks*